United States Patent
Jin et al.

(10) Patent No.: US 11,389,668 B2
(45) Date of Patent: Jul. 19, 2022

(54) IMMUNE DOSE COMPUTATION FOR TREATMENT PLAN OPTIMIZATION IN RADIOTHERAPY

(71) Applicant: The Trustees of Indiana University, Indianapolis, IN (US)

(72) Inventors: Jian-Yue Jin, Indianapolis, IN (US); Feng-Ming Kong, Indianapolis, IN (US); Hong Zhang, Wilmington, DE (US); Huan Yao, Indianapolis, IN (US)

(73) Assignee: The Trustees of Indiana University, Indianapolis, IN (US)

( * ) Notice: Subject to any disclaimer, the term of this patent is extended or adjusted under 35 U.S.C. 154(b) by 159 days.

(21) Appl. No.: 16/968,849

(22) PCT Filed: May 2, 2018

(86) PCT No.: PCT/US2018/030609
§ 371 (c)(1),
(2) Date: Aug. 10, 2020

(87) PCT Pub. No.: WO2019/160571
PCT Pub. Date: Aug. 22, 2019

(65) Prior Publication Data
US 2021/0016107 A1    Jan. 21, 2021

Related U.S. Application Data

(60) Provisional application No. 62/630,015, filed on Feb. 13, 2018.

(51) Int. Cl.
*A61N 5/10* (2006.01)

(52) U.S. Cl.
CPC ................................ *A61N 5/1031* (2013.01)

(58) Field of Classification Search
CPC . A61N 5/00; A61N 5/10; A61N 5/103; A61N 5/1031
See application file for complete search history.

(56) References Cited

U.S. PATENT DOCUMENTS

2004/0008822 A1    1/2004    Bortfeld et al.
2016/0339270 A1    11/2016   Ellsworth et al.

FOREIGN PATENT DOCUMENTS

WO         2016140955 A1    9/2016

OTHER PUBLICATIONS

International Search Report and Written Opinion, ISA/US Commissioner for Patents, dated Jul. 23, 2018, for International PCT Application No. PCT/US2018/030609.

*Primary Examiner* — Jurie Yun
(74) *Attorney, Agent, or Firm* — Faegre Drinker Biddle & Reath LLP

(57) ABSTRACT

Methods for calculating the radiation dose to the immune system of a patient undergoing radiotherapy are provided. In particular, the methods provide for calculating an effective dose to blood (EDIC) to circulating immune cells. The methods can be incorporated into radiotherapy (RT) treatment planning systems, which are also provided. The methods can be used to optimize patient treatment plans. Methods for treating a patient with RT with an optimized treatment plan are provided.

35 Claims, 12 Drawing Sheets

IMMUNE DOSE COMPUTATION FOR TREATMENT PLAN OPTIMIZATION IN RADIOTHERAPY

CROSS-REFERENCE TO RELATED APPLICATIONS

This application is the National Stage of International Patent Application No. PCT/US2018/030609, filed May 2, 2018, which claims priority to U.S. Provisional Patent Application No. 62/630,015, filed Feb. 13, 2018, the contents of each of which are expressly incorporated herein by reference in their entireties.

STATEMENT OF GOVERNMENT SUPPORT

This invention was made with government support under CA142840 awarded by the National Institutes of Health. The Government has certain rights in the invention.

BACKGROUND

Radiotherapy (RT) is a major modality for cancer treatment. In radiotherapy, the tumor and normal organs within the paths of radiation fields are often delineated in a computed tomography (CT) image, and radiation doses to the tumor and these organs at risk (OARs) are calculated. Treatment plan optimization can be performed to maximize the radiation dose to the tumor while minimizing the dose to the OARS.

Recent reports suggest that radiation-induced tumor cell killing can activate the immune system by releasing tumor specific antigens. Preclinical studies have demonstrated that the immune system plays a key role in tumor control during RT. Treatments with RT alone or RT combined with immunotherapy have been observed to control tumors in immunocompetent mice, but not in immune-deficient mice. An abscopal effect (i.e., shrinkage of un-irradiated tumors far apart from the RT fields) has been observed in animal studies and in a single-patient case report. While these observations suggest that RT may augment anti-tumor immunity in certain settings, RT is also well known to have immunosuppressive effects. One of the most common and clinically significant features of radiation-induced immunosuppression is radiation-induced lymphopenia which has been repeatedly associated with poorer survival in several studies as well as in a recent pooled analysis of multiple treatment-refractory solid tumors.

Despite these observations, the immune system has not generally been considered as an OAR.

SUMMARY

In a first aspect, described herein is a radiotherapy system comprising a radiotherapy device configured to deliver a radiotherapy to a patient and a treatment controller having one or more processors and a non-transitory, tangible storage medium containing instructions that, when executed, cause the one or more processors to: calculate from an initial radiotherapy treatment plan for a patient, an equivalent uniform dose (EUD) for each organ in a target irradiation area in the patient; calculate an effective dose of radiation to circulating immune cells in blood (EDIC) for the patient by summing all EUDs for all organs in the target irradiation area; and generate a new patient-specific radiotherapy treatment plan for the patient, wherein the new patient-specific radiotherapy treatment plan decreases a calculated EDIC relative to the initial radiotherapy treatment plan, wherein the radiotherapy device is configured to deliver radiotherapy to the patient according to the new patient-specific radiotherapy treatment plan.

In some embodiments, the radiotherapy system of claim 1 further comprises one or more imaging modalities.

In some embodiments, the instructions, when executed, cause the one or more processors to generate one or more additional new patient-specific radiotherapy treatment plans for the patient during delivery of the new patient-specific radiotherapy treatment plan to the patient.

In a second aspect, described herein is a method for treating a patient, the method comprising: calculating from an initial radiotherapy treatment plan for the patient, an equivalent uniform dose (EUD) for each organ in a target irradiation area in the patient; calculating an effective dose of radiation to circulating immune cells in blood (EDIC) for the patient by summing all EUDs for all organs in the target irradiation area; generating a new patient-specific radiotherapy treatment plan for the patient, wherein the new patient-specific radiotherapy treatment plan decreases a calculated EDIC relative to the initial radiotherapy treatment plan; and delivering radiotherapy to the patient according to the new patient-specific radiotherapy treatment plan.

In some embodiments, the method for treating a patient further comprises acquiring an image of the target irradiation area in the patient utilizing at least one imaging modality.

In some embodiments, the method for treating a patient further comprises generating one or more additional new patient-specific radiotherapy treatment plans for the patient during delivery of the new patient-specific radiotherapy treatment plan to the patient, stopping delivery of the new patient-specific radiotherapy treatment plan to the patient, and delivering one of the one or more additional new patient-specific radiotherapy treatment plans.

In a third aspect, described herein is a radiotherapy system comprising a radiotherapy device configured to deliver radiotherapy in accordance with a radiotherapy plan and one or more processors programmed to perform a method for treating a patient described herein.

In a fourth aspect, described herein is non-transitory computer-readable medium having instructions stored thereon for causing one or more processors to perform

Figure 1:
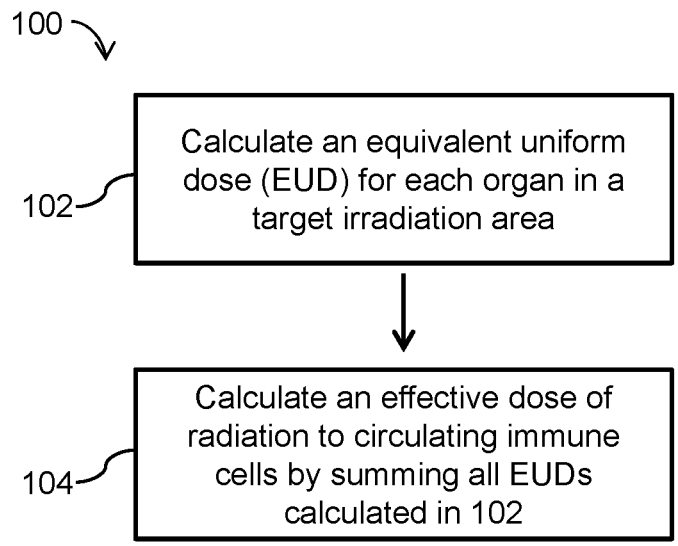
FIG. 1 is a flowchart illustrating a method according to one embodiment.

While the disclosed subject matter is amenable to various modifications and alternative forms, specific embodiments are described herein in detail. The intention, however, is not to limit the disclosure to the particular embodiments described. On the contrary, the disclosure is intended to cover all modifications, equivalents, and alternatives falling within the scope of the disclosure as defined by the appended claims.

Similarly, although illustrative methods may be described herein, the description of the methods should not be interpreted as implying any requirement of, or particular order among or between, the various steps disclosed herein. However, certain embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

As the terms are used herein with respect to ranges, "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error, differences in measurement and/or manufacturing equipment calibration, human error in reading and/or setting measurements, adjustments made to optimize performance and/or structural parameters in view of differences in measurements associated with other components, particular implementation scenarios, imprecise adjustment and/or manipulation of objects by a person or machine, and/or the like.

DETAILED DESCRIPTION

Certain embodiments described herein provide methods for calculating the radiation dose to the immune system of a patient undergoing radiotherapy. In some embodiments, the methods described herein can be incorporated into radiotherapy (RT) treatment planning systems, which are also provided herein. In some embodiments, the methods described herein can be used to optimize patient treatment plans. Also provided are methods for treating a patient with RT with an optimized treatment plan.

As discussed below in more detail, portions of these methods can be implemented using a processor executing software stored in a tangible, non-transitory storage medium. For example, the software could be stored in the long-term memory (e.g., solid state memory) in a radiotherapy system, executed by the processor(s) in the radiotherapy system. In other embodiments, the software could be stored in a separate system.

The immune system has largely not been considered as an organ at risk for RT toxicity, and no guidelines presently exist to delineate the immune system for the purposes of RT planning. In certain embodiments, the immune system is defined as a composition of six substructures: 1) immune cells in the lymph nodes and parenchyma in the organ of the tumor site; such as in lung lymph nodes and lung parenchyma for lung cancer; 2) immune cells in the circulating blood; 3) immune cells in the lymph nodes and other major lymphatic organs in the other parts of the body, including lymphatic ducts and spleen; 4) T-cells in the thymus; 5) Bone marrow; and 6) tumor infiltrating immune cells within the tumor. As described herein, the radiation dose to the immune system is a key predictor for success of treatment. While the immune cells in 5 of the 6 substructures are relatively stable during irradiation, the immune cells in the circulating blood are not stable. Calculating the radiation dose administered to this substructure is very difficult.

To date, few examples of methods for calculating the radiation dose received by the immune system during RT exist. One method, described by Ellsworth et al. (US Pat. Pub. No. 2016/0339270), determines a dose received by circulating blood as the dose to the immune system during RT. The method predicts a radiation dose received by the circulating blood by assuming the blood has a similar known flow rate in an irradiating site that includes a tumor and surrounding normal tissues, determining a dose of radiation delivered to the site in a patient, generating a three-dimensional dose grid for the site, using the three-dimensional dose grid for the site to calculate a distribution of radiation dose to a blood pool that is either within or transits through the site, generating dose volume histograms for the blood or its constituents as normal organs; and indicating the dose of radiation received by circulating blood using the quantification.

The method of Ellsworth et al. assumes that the blood concentration and flow rate through the irradiating site that includes the tumor and surrounding normal tissue are the same. However, the blood concentration and flow rate through the various organs and vessels in the irradiating site vary considerably. As described herein, the blood concentration and flow rate are important determinants of the radiation absorbed by the circulating immune cells in blood.

In addition, the immune system also includes other substructures than the circulating immune cells in blood. Thus, the present disclosure provides improved methods to more accurately determine the radiation dose received by the circulating immune cells in blood and immune system during RT. Furthermore, described herein for the first time are methods for identifying a radiation dose to the immune system that can improve overall survival of patients receiving radiotherapy.

Certain embodiments provide methods for calculating an effective dose of radiation to circulating immune cells in blood (EDIC) in a patient. As depicted in FIG. 1, in some embodiments, method 100 for calculating the EDIC comprises first calculating an equivalent uniform dose (EUD) 102 to the total blood after n fractions as a result of circulating through an organ and/or vascularized tumor in a target irradiation area including one or more tumors in the patient and then summing all calculated EUDs 102 for the target irradiation area. The target irradiation area includes the tumor that is being targeted by RT, as well as various surrounding normal organs in the pathway of the irradiating fields. For example, in an embodiment where the lungs are to be treated by R, the organs to be included in the target irradiation area include the lungs, the heart, the large vessels of the thoracic region, and the small vessels and capillaries of the tumor and other organs in the thoracic region. In this example, the EDIC is calculated 104 by summing the calculated EUDs for the total blood circulating through the lungs, heart, large vessels of the thoracic region, and the small vessels and capillaries of the tumor and other organs in the thoracic region (see also FIG. 3).

In some embodiments, the EUD to the total blood circulating through each organ and/or vascularized tumor can be calculated as described by Niemierko (*Med Phys*, 1997, 24(1):103-110), which is hereby incorporated by reference in its entirety, and can be calculated directly from the corresponding dose-volume histograms (DVHs).

Figure 2:
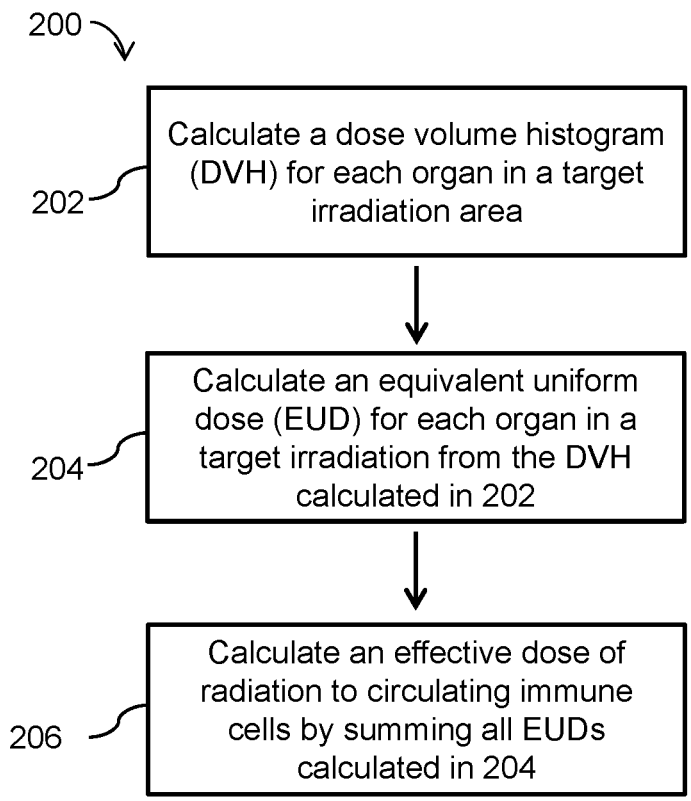
FIG. 2 is a flowchart illustrating a method according to one embodiment.
Figure 10:
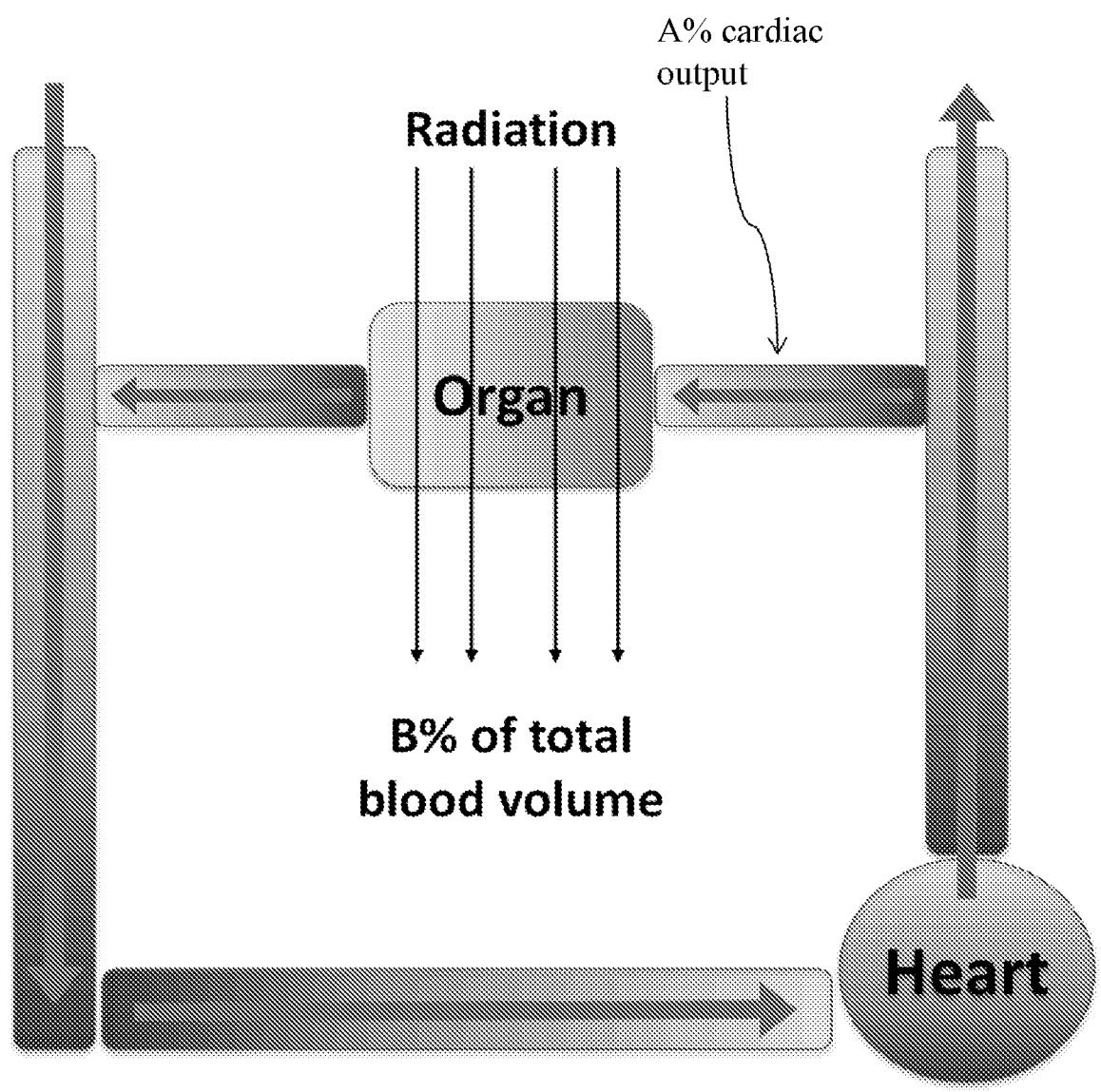
FIG. 10 is an illustration depicting the defined parameters of: percentage of cardiac output (A %); and percentage of blood volume (B %), in accordance with embodiments of the disclosure.

In certain embodiments, a novel method for calculating the EUD for each organ and/or vascularized tumor is used. As depicted in FIG. 2, according an embodiment 200, the DVH of the total circulating blood (or immune cells in the circulating blood) due to irradiation of an organ is first determined 202. To determine the DVH, it is assumed that the irradiation uniformly delivers a dose (d) to the portion of blood that passes through the organ during a treatment fraction, which account for V % of the total circulating blood. V % is calculated by:

$$V\% = B\% + (A\% - B\%)*t/T, \quad (1)$$

wherein the organ has 1) a cardiac output A %, which is defined as the amount of blood branching into the organ as a percentage of the total blood flow out of the heart, and 2) a percentage blood volume B %, which is defined as the amount of blood contained in the organ at any time relative to the total body blood volume, that the time for completing one blood circulation is T, and the irradiation time is t. These definitions of A % and B % are illustrated by FIG. 10, which depicts a theoretical organ having a cardiac output A % and a percentage blood volume B %. The dose delivered to V % is given by:

$$d = \left(\frac{MOD}{n}\right) * \left(\frac{B}{V}\right), \quad (2)$$

wherein the number of radiotherapy fractions is n, and the organ has received a mean organ dose of MOD. In certain embodiments, it is assumed that after each irradiation, the irradiated immune cells are uniformly redistributed before the next radiotherapy fraction is delivered. Thus, the differential DVH after ith fraction can be derived by calculating V(i,j), which is the percentage of blood volume that receives a dose of j*d. Initially, V(0,0)=100%.

After the $1^{st}$ fraction, V(1,1)=V %*V(0,0), and V(1,0)=(1−V %)*V(0,0).

After the $2^{nd}$ faction, V(2,2)=V %*V(1,1), V(2,1)=V %*V(1,0)+(1−V %)*V(1,1) and V(2,0)=(1−V %)*V(1,0).

After $n^{th}$ fraction, V(n,n)=V %*V(n−1,1), V(n, n−1)=V %*V(n−1,n−2)+(1−V %)*V(n−1,n−1), . . . V(n,1)=V %*V(n−1,0)+(1−V %)*V(n−1,1), and V(n,0)=(1−V %)*V(n−1, 0).

In some embodiments, the equivalent uniform dose (EUD) to the total blood occurring as a result of irradiation of an organ within the target irradiation area is calculated from the differential DVH 204. In certain embodiments, known algorithms can be used to calculate the EUD from the differential DVH. For example, the EUD can be calculated by:

$$EUD_n = [\Sigma_j V(n,j)*(d*j)^a]^{1/a}, \quad (3)$$

(Niemierko (*Med Phys*, 1997, 24(1):103-110)). The EDIC can then be calculated 206 by summing all calculated EUDs for the irradiation area.

Figure 8A:
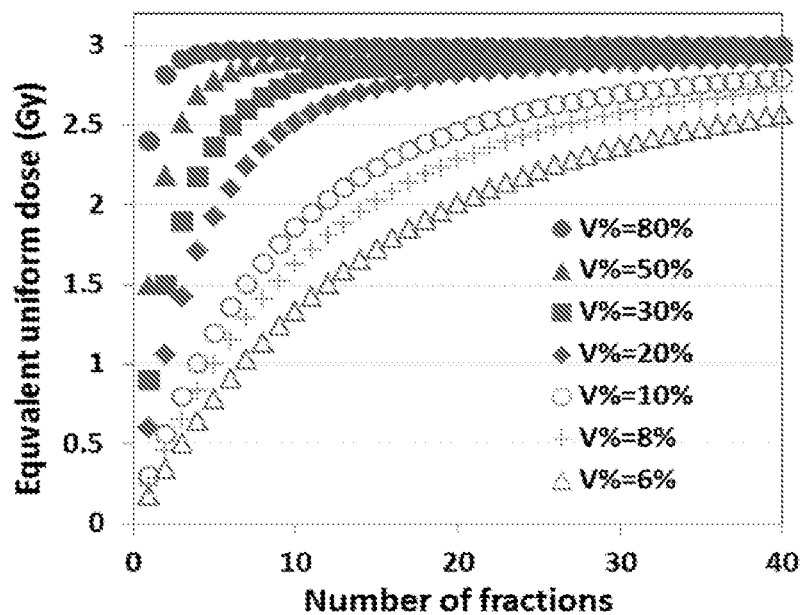
FIGS. 8A and 8B depict graphs demonstrating the variation in equivalent uniform dose (EUD) to the total blood as a function of the fraction number (n) for various V % (the percentage blood volume irradiated in each fraction for a specific organ), which contains B % of blood volume and received irradiation with a mean organ dose (MOD).

In some embodiments, the EUD of the blood contributed by a given blood-containing organ can be calculated for various V %. As depicted by FIG. 8A, the calculated EUD varies with fraction number n for various V % for an exemplary organ with B %*MOD=3 Gy. FIG. 8A demonstrates that when n>2.4/V %, the EUD starts to saturated, indicating that the entire blood volume becomes irradiated when the number of fractions (n) is sufficiently large.

Figure 8B:
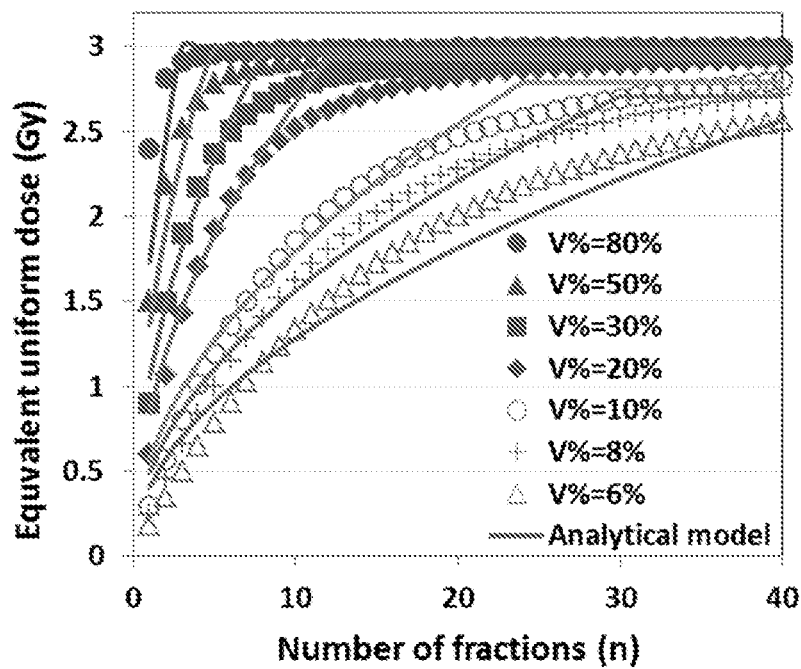
Figure 11:
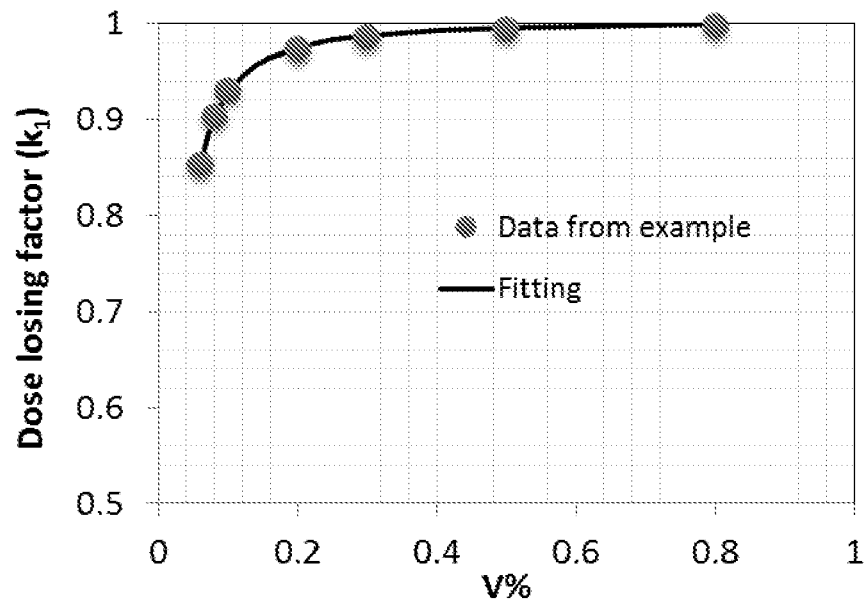
FIG. 11 depicts a graph demonstrating a relationship between dose losing factor $k_1$ and V %, in accordance with embodiments of the disclosure.
Figure 12:
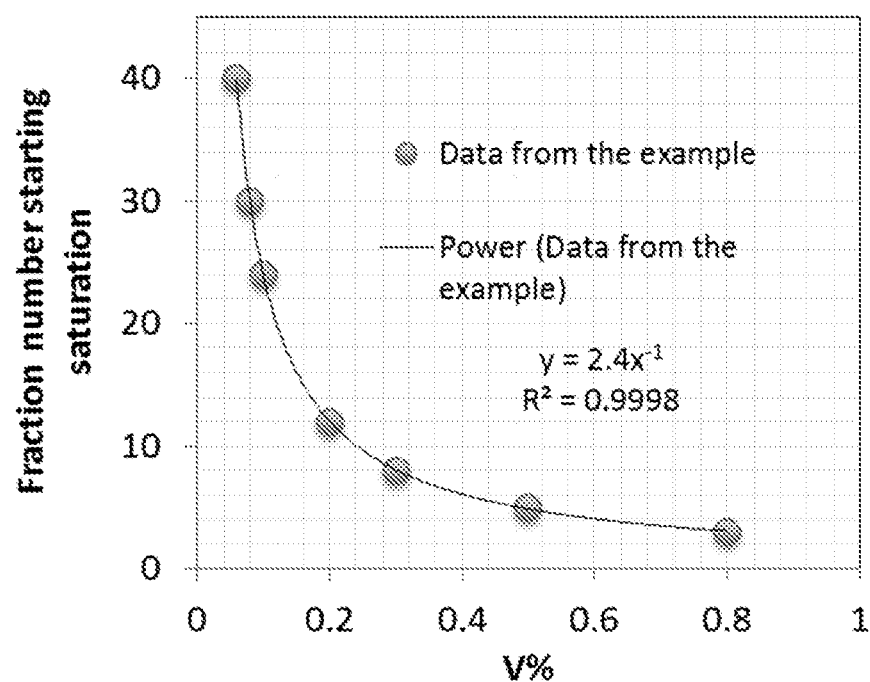
FIG. 12 depicts a graph demonstrating a relationship between the fraction number at which saturation occurs and V %, in accordance with embodiments of the disclosure.

In some embodiments, the EUD can be approximated by an analytical model:

$$EUD = B\% * MOD * k_1 \text{ when } n > k_2, \text{ or} \quad (4a)$$

$$EUD = B\% * MOD * k_1 * \left(\frac{n}{k_2}\right)^{\frac{1}{2}} \text{ when } n < k_2, \quad (4b)$$

wherein $k_1$ and $k_2$ depend on V %. $k_1$ is a dose losing factor, and $k_1$ can be approximated by $k_1=1+0.0031*\ln(V\%)/V\%$ (see FIG. 11). $k_2$ is a saturation fraction factor, and can be approximated by $k_2=2.4/V\%$ (see FIG. 12). FIG. 8B depicts the difference in EUD between the EUD model of (4a) and (4b), and the actual EUD as determined from the DVH. As demonstrated by FIG. 8B, the models provide an excellent determination of EUD.

Figure 8C:
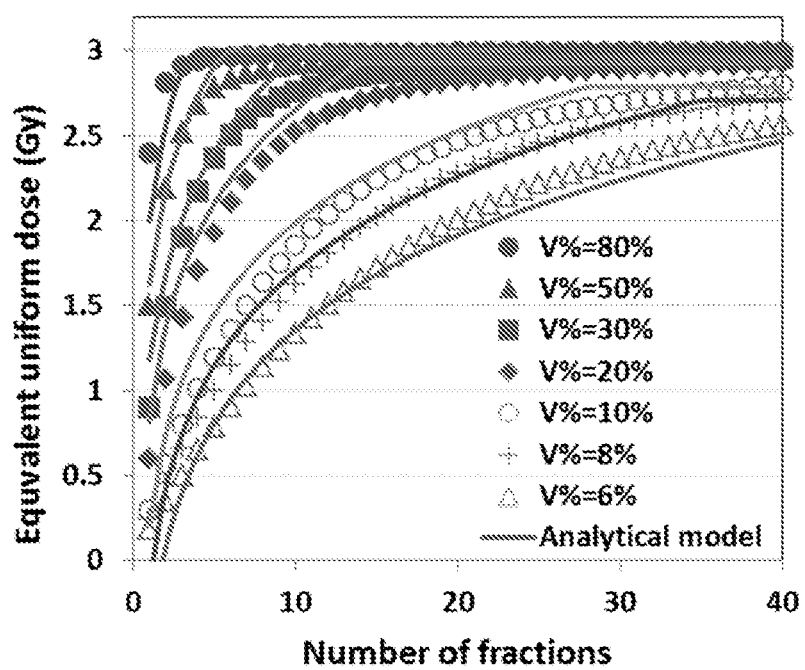
FIG. 8C depicts the difference in EUD between an EUD model and the actual EUD as determined from the DVH, in accordance with embodiments of the disclosure.

In some embodiments, the EUD can be alternatively approximated by other analytical models such as:

$$EUD = B\% * MOD * k_1 \text{ when } n > k_2, \text{ and} \quad (5a)$$

$$EUD = B\% * MOD * k_1 + 0.8 * \ln\left(\frac{n}{k_3}\right) \text{ when } n < k_2, \quad (5b)$$

wherein $k_1=1+0.0031*\ln(V\%)/V\%$, as described above, and $k_3$ is a saturation fraction factor, and can be approximated by $k_3=2.8/V\%$. FIG. 8C depicts the difference in EUD between the EUD model of (5a) and (5b), and the actual EUD as determined from the DVH. As demonstrated by FIG. 8C, the models provide an excellent determination of EUD.

In some embodiments, the saturation fraction factor is related to the number of radiation fractions required to saturate the EUD, indicating that the entire blood volume becomes irradiated. In certain embodiments, the saturation fraction factor is the quotient of a numerator of 2 to 3 and a denominator equal to V %. As provided above, in some embodiments, the saturation fraction factor $k_2=2.4/V$ %. In some embodiments, the saturation fraction factor $k_3=2.8/V$ %.

Figure 3:
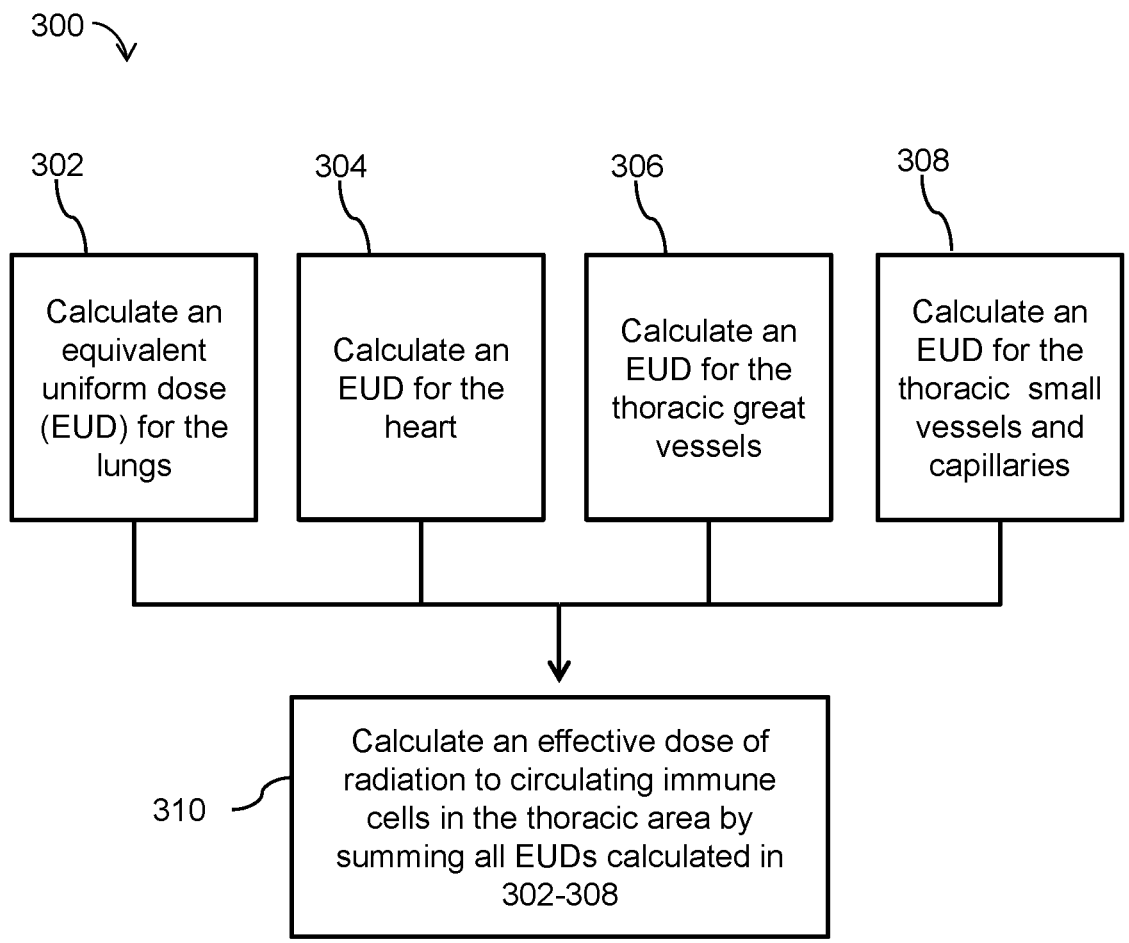
FIG. 3 is a flowchart illustrating a method according to one embodiment.

FIG. 3 illustrates the EDIC calculation for a patient in which the lungs are to be treated (i.e., thoracic radiation). The EUD for each of the lungs 302, heart 304, thoracic great vessels 306, and thoracic small vessels and capillaries 308 is first calculated, and then summed to determine the EDIC 310.

In some embodiments, an EDIC for a proposed or prospective RT treatment plan can be calculated. The EDIC for a RT treatment plan selected for a patient that is scheduled to undergo RT treatment can be calculated prior to treatment to determine the radiation dose to be administered to the patient. Depending on the calculated EDIC, treatment can proceed according to the selected treatment plan, the selected treatment plan can be optimized, or a new treatment plan can be selected. Methods for selecting and/or optimizing an initial RT treatment plan are provided herein. In other embodiments, an EDIC for an RT treatment plan already administered to a patient can be calculated.

Figure 9:
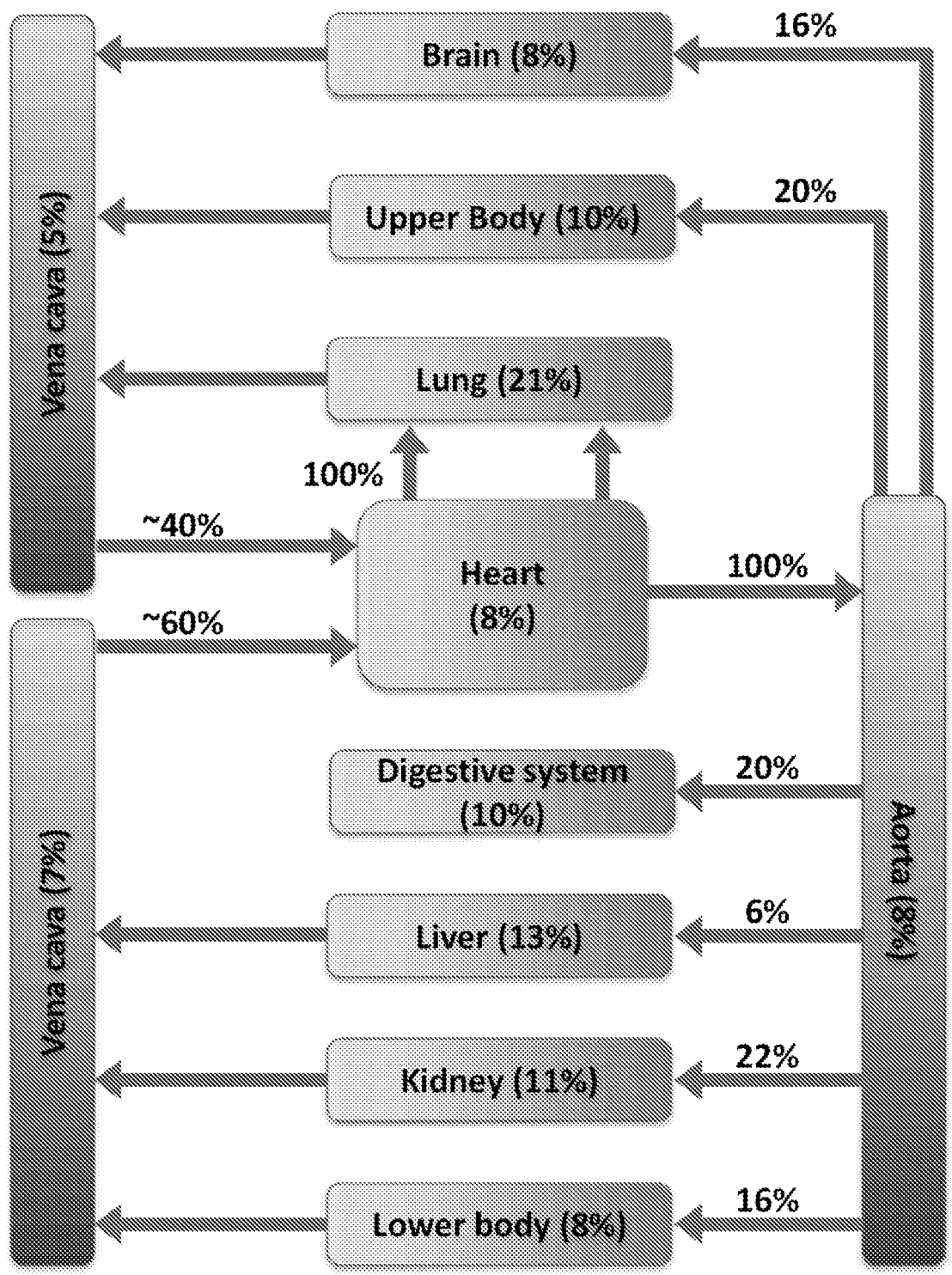
FIG. 9 is a schematic representation of the major organs in the circulatory system and their estimated percentage of cardiac output (A %) and percentage of blood volume (B %) according to established anatomy and physiology data.

The values for A % and B % for various organs for use according to some embodiments are provided in Table 1, and depicted in FIG. 9. In other embodiments, the values for A % and B % can be calculated based on known population data. In some embodiments, the values for A % and B % can be calculated for a patient based on the patient's specific anatomy. In some embodiments, information on the patient's specific anatomy can be provided by one or more imaging modalities, including, for example, computed tomography (CT) scanners, positron emission tomography (PET) scanners, magnetic resonance (MR) scanners, single photon emission computed tomography (SPECT) scanners, and the like.

TABLE 1

| Organ | A% (% cardiac output) | B% (% total blood volume) |
|---|---|---|
| Brain | 16 | 8 |
| Upper Body | 20 | 10 |
| Lungs (total) | 100 | 12 |
| Lung (each) | 50 | 6 |
| Heart | 100 | 8 |
| Digestive System | 20 | 10 |
| Liver | 6 | 13 |
| Kidneys | 22 | 11 |
| Lower Body | 16 | 8 |
| Great Vessels | 30-60 | Dependent on contoured volume |

Returning to the example of thoracic radiation, the organs/components that are irradiated mainly include 1) the lungs, 2) the heart, 3) the great vessels, and 4) small vessels and capillaries in other organs, such as the esophagus, muscles, bones, and skin. The total dose to the circulating immune cells resulting from thoracic radiation can be considered as the sum of EUDs to the total blood contributed by these four organs/components. Assuming T~1 min, t>1 min, and n≥30 (as most conventional definitive radiotherapy requires more than 30 fractions, EUD to total blood can be reliably calculated as B %*MOD for lung hear, and great vessels, because of their large cardiac outputs (A % is 50% for each lung, 100% for heart, >30% for the great vessels). B % is 12% for lung, 8% for heart, 45%-50% for the great vessels, and 30%-40 for the small vessels and capillaries in other organs. For the $4^{th}$ component (small vessels and capillaries in other organs), V % can be estimated as being 6-8%. Thus $k_1$~0.85, $k_2$~45, and EUD to the total blood can be estimated using equation 4. It can be assumed that the vessels and capillaries are uniformly distributed in the body, so that integral total body dose can be used to replace the MOD for the large vessels as well as the $4^{th}$ component (i.e., small vessels and capillaries in other organs). Therefore, the EDIC, as the sum of EUD contributions of the 4 components, is expressed as:

$$EDIC = B_1\% * MLD + \qquad (6)$$
$$B_2\% * MHD + \left[B_3\% + B_4\% * k_1 * \left(\frac{n}{k_2}\right)^{\frac{1}{2}}\right] * ITD/(61.8*10^3),$$

wherein MLD, MHD, and ITD are mean lung dose, mean heart dose, and integral total dose, respectively, and $61.8*10^3$ (cm$^3$) is the average total body volume, assuming average weight and density of 70 lps/63 kg and 1.02 g/cm$^3$.

Alternatively, in the thoracic RT example, the EUD to the total blood resulting from circulation through the large vessels can be calculated as $$EUD = \frac{V_{GV}}{5000} * MVD,$$

wherein $V_{GV}/5000$ is the percentage blood volume in the contoured great vessels, with $V_{GV}$ as the volume of contoured great vessels in cubic centimeters and 5000 as the total blood volume, giving:

$$EDIC = B_1\% * MLD + B_2\% * MHD + \qquad (7)$$
$$\frac{V_{GV}}{5000} * MVD + B_4\% * k_1 * \left(\frac{n}{k_2}\right)^{\frac{1}{2}} * ITD/(61.8*10^3)$$

The EDIC calculation for a thoracic radiotherapy is provided merely as an example. It will be recognized that an EDIC can be calculated for other target irradiation areas, including those irradiated during the treatment of, for example, brain cancer, non-melanoma skin cancer, head and neck cancer, breast cancer, cervical cancer, rectal cancer, liver cancer, pancreatic cancer, and prostate cancer. In such target irradiation areas, the EUDs to the blood circulating through the irradiated organs and/or other components can be calculated from a differential DVH for each of the organs and/or other components, or can be approximated as provided by either equation 4 or 5. Necessary assumptions, such as those made for the small vessels and capillaries in the thoracic RT example, will be recognized by those of skill in art, and are within the scope of the present disclosure. For example, for a tumor in the pancreas, the radiation will potentially pass through the liver, the kidney, the digestive system, the great vessels, and all the other organs. The mean organ dose for these organs can be calculated, the A % and B % of these organs can be determined according to table 1, and based on the estimated irradiation time for each fraction, we can determine the V % for each organ, thus an estimated EDIC can be calculated using EQ. 6 or EQ. 7.

The parameters provided by Table 1, EQs. 6 and 7, such as B1%, B2%, B3%, B4%, 5000 (ml) for the total blood volume, and $61.8*10^3$ for the body mass can be individualized for different patients according to their weight, and volumes as determined by their CT image.

It is described herein for the first time that there is a relationship between EDIC as calculated by the methods described herein, and overall survival; hazard rates increase with increasing EDIC when EDIC is less than 6.0 Gy or larger than 8.0 Gy. The curve is relatively flat when EDIC is between 6.0 Gy and 8.0 Gy.

In certain embodiments, an RT treatment plan resulting in a predicted EDIC of 6.0 Gy or less is selected for a patient. The RT treatment plan resulting in a predicted EDIC of 6.0 Gy or less can be selected from a plurality of potential RT treatment plans. In certain embodiments, the RT treatment plan having the lowest EDIC is selected. In other embodiments, the RT treatment plan having the best predicted outcome while maintaining an EDIC of 6.0 Gy is selected. In certain embodiments, RT is administered to a patient according to the selected RT treatment plan.

Figure 4:
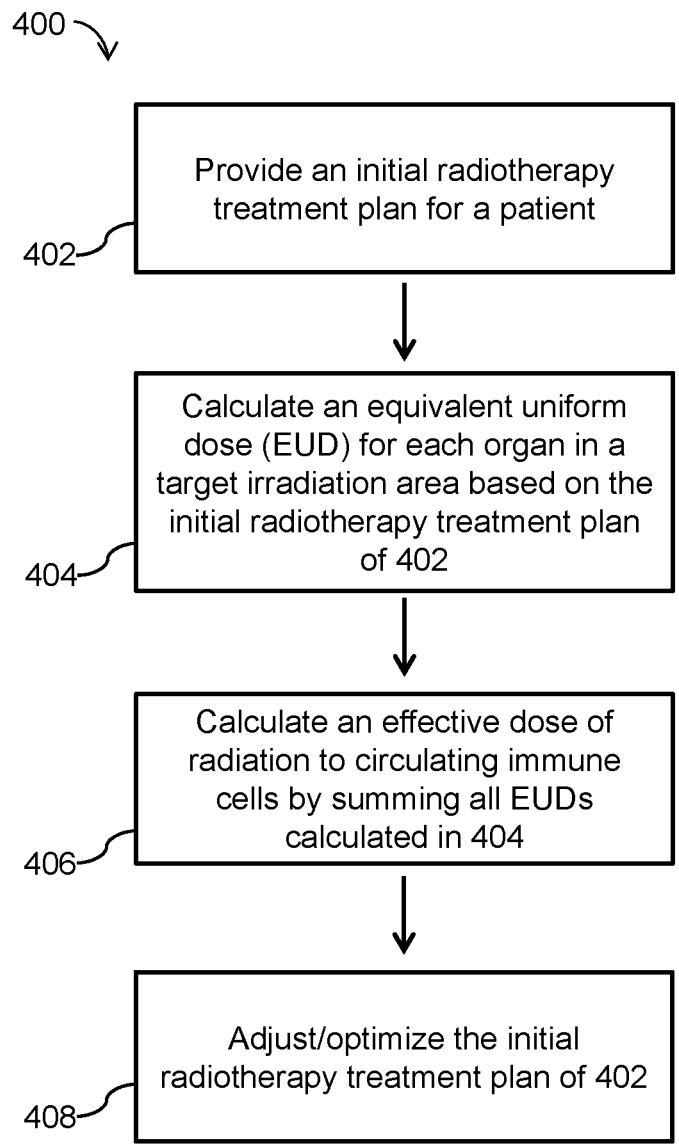
FIG. 4 is a flowchart illustrating a method according to one embodiment.

Certain embodiments provide methods for generating a patient-specific radiotherapy treatment plan. FIG. 4 illustrates a general method 400 for generating a patient-specific radiotherapy treatment plan. An initial RT treatment plan for a patient is provided 402. An EUD for each organ in the target irradiation area based on the initial RT treatment plan is then calculated 404, and the EDIC is calculated 406 by summing all EUD's calculated for the target irradiation area. Based on the EDIC, the initial RT treatment plan is then adjusted or otherwise optimized 408.

In some embodiments, a patient-specific RT treatment plan can be generated. In some embodiments, a new patient-specific RT treatment plan is generated. In certain embodiments, a new patient-specific RT treatment plan is generated by adjusting or otherwise optimizing an initial RT treatment plan preselected for a patient. In certain embodiments, the initial RT treatment plan is adjusted to reduce the calculated EDIC and generate a new patient-specific RT treatment plan with a lower calculated EDIC. In some embodiments, any reduction in EDIC can have an impact on overall survival. In some embodiments, the new patient-specific RT treatment plan has a calculated EDIC of 6.0 Gy or less. In other embodiments, the new patient-specific RT treatment plan maximizes the radiation dose while maintaining a calculated EDIC of 6.0 Gy or less. The EDIC for any particular RT treatment plan can be calculated as provided herein, where the treatment parameters of a particular RT treatment plan are incorporated into the EDIC calculation.

In certain embodiments, a new patient-specific RT treatment plan having a reduced calculated EDIC relative to an initial RT treatment plan can be generated by, for example, reducing circulating blood exposure via hypofractionated treatment regimens and/or decreasing the radiation delivery time (i.e., increasing the dose rate) relative to the initial RT treatment plan; adjusting beam energies and directions, number of beams, and/or collimator margins relative to the initial RT treatment plan, and/or using intensity modulated radiotherapy (IMRT) and other similar advanced planning techniques such as volumetric modulated arc therapy (VMAT); using advanced RT technology such as, for example, image guided adaptive therapy and proton therapy; and dose de-escalation and margin reduction relative to the initial RT treatment plan. Such techniques can reduce the calculated EDIC relative to the initial RT treatment plan, and may thus improve overall survival of patients undergoing radiotherapy treatment using a new patient-specific RT treatment plan determined according to the methods of the disclosure.

In other embodiments, a new patient-specific RT treatment plan maximizes the radiation does delivered to a tumor while minimizing the dose to the circulating immune cells (i.e., minimizing EDIC). In some embodiments, such optimization may necessitate increasing the calculated EDIC in order to maximize the radiation dose delivered to a tumor. Any increase in the dose to the circulating immune cells must be weighed against any benefit derived from maximizing the radiation dose to the tumor. In some embodiments, the new patient-specific RT treatment plan is set so that the calculated EDIC increases, but does not exceed 6.0 Gy. This may be desirable to allow for maximization of the radiation dose to a tumor while minimizing the risks associated with higher doses being administered to the circulating immune cells. The EDIC can be increased by, for example, increasing the radiation delivery time, adjusting beam energies and directions, the number of beams, and collimator margins, and dose escalation and increasing margins.

In some embodiments, the radiation dose to the immune cells in the lymph nodes and parenchyma of the site of the tumor can be surrogated by the radiation dose to the organ of the tumor site, or the dose to the lymphatic stations in the site. For example, for lung tumors, the dose to the lung or the dose to the lung lymphatic station can be the surrogate for the radiation dose to the immune cells in the lymph nodes.

In some embodiments, the radiation dose to the tumor infiltrating immune cells within the tumor can be determined as $D=D_0-T_a$, wherein the $D_0$ is the prescription dose to the tumor, and $T_a$ is the dose that begins to activate the anti-tumor immunity.

In some embodiments, the radiation dose to the immune cells in the lymph nodes and other major lymphatic organs in the other parts of the body can be determined by directly delineating the structures (lymphatic ducts, spleen, etc.) in a patient's CT images and calculating the dose to the structures.

In some embodiments, the radiation dose to the T-cells in the thyme can be determined by directly delineating the thyme structure in a patient's CT image and calculating the dose to the thyme.

In some embodiments, the radiation dose to the bone marrow can be determined by directly delineating the bone structure in a patient's CT image and calculating the dose to the structure.

Figure 13:
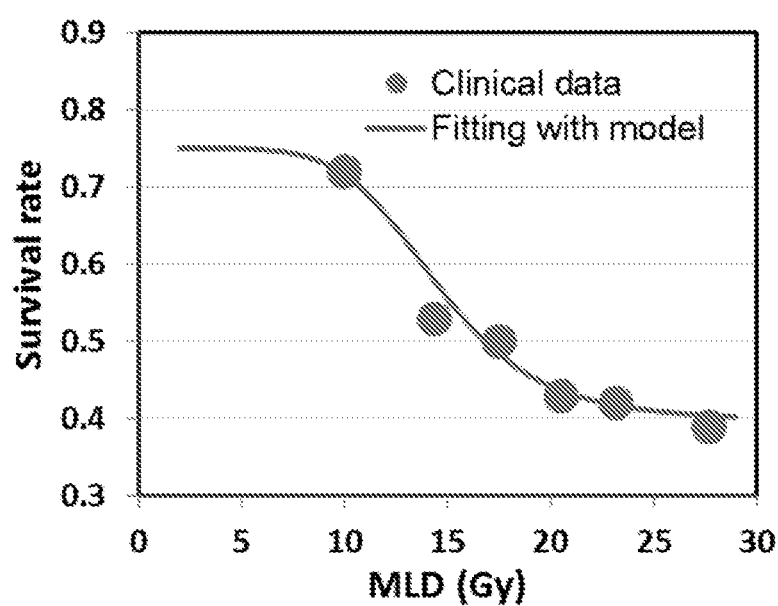
FIG. 13 depicts a graph demonstrating a relationship between the survival rate and mean lung dose (MLD), in accordance with embodiments of the disclosure.

It is described herein for the first time that the relationship of overall survival (OS) and mean lung dose (MLD) can be modeled by a normal tissue complication probability (NTCP) model with $D_{50}=15$ Gy, and the OS did not go to 0% when MLD further increased (FIG. 13). Although MLD has been reported to be associated with OS, it was previously believed that the lung toxicity was the underlying mechanism of this association. However, the fatal lung toxicity usually occurred when lung doses were much higher (e.g., it has been reported that $D_{50}$ of MLD for grade 2 toxicity was about 30 Gy). The OS-MLD relationship is well explained by the radiation damage of the immune cells in the lung lymph nodes and lung parenchyma. The immune cell pools in blood and other substructures may provide continuous flow to the site, so that the OS did not go to 0%.

In certain embodiments, methods are provided for determining a dose-volume histogram (DVH) for the total circulating blood (or immune cells in the circulating blood). In some embodiments, the DVH for the immune cells in the circulating blood is determined as provided herein. While in certain embodiments the DVH for the immune cells is first determined in order to provide for the calculation of the equivalent uniform dose (EUD) to the immune cells in the circulating blood, in other embodiments no EUD is calculated, and the DVH for the immune cells in the circulating blood can be utilized as a radiotherapy treatment plan evaluation tool. In certain embodiments, the DVHs for two or more different radiotherapy treatment plans are determined and evaluated. The radiotherapy treatment plan providing a desired radiation dose distribution to the immune cells in the circulating blood can then be selected.

Figure 5:
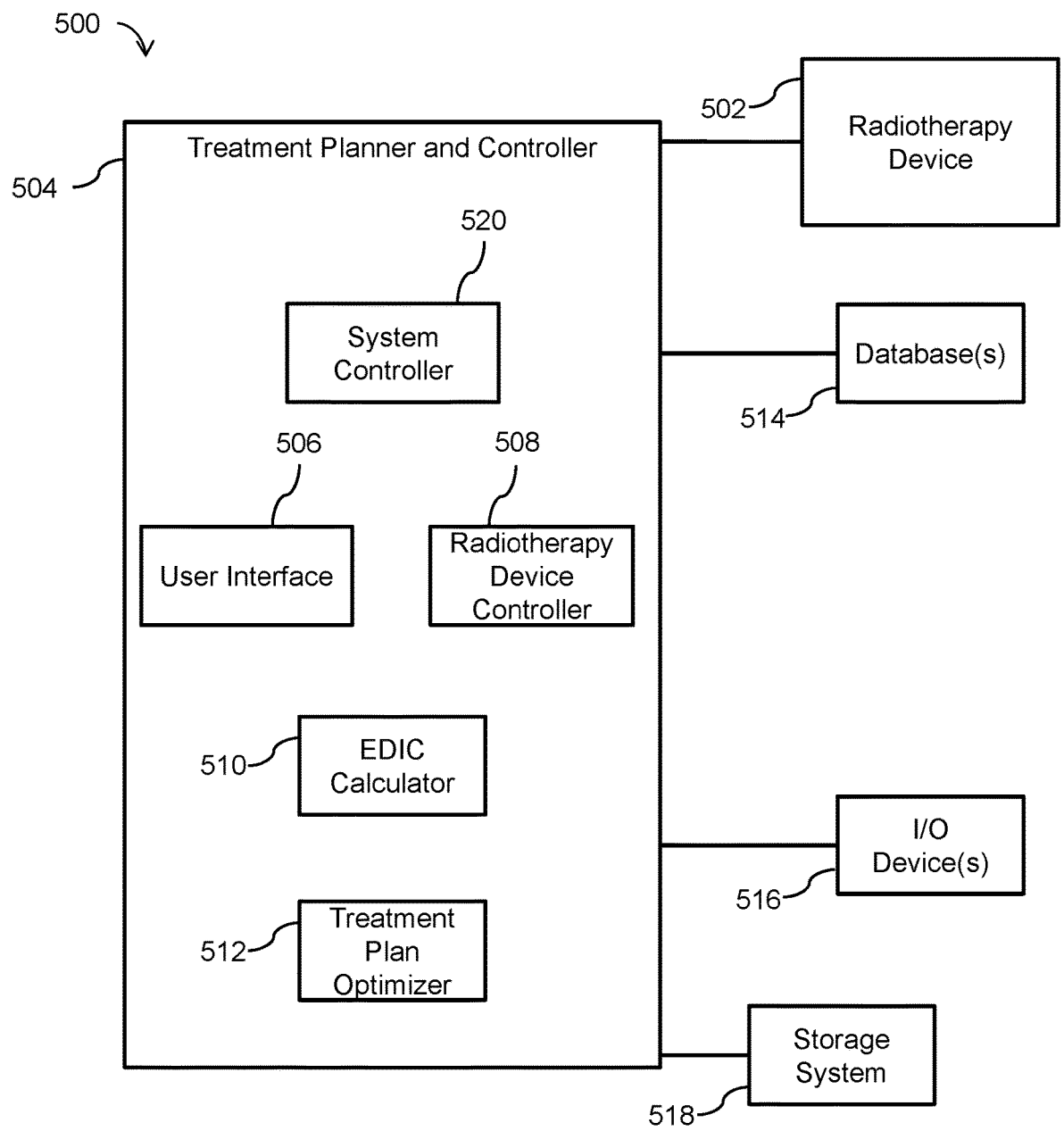
FIG. 5 is a block diagram illustrating a system formed in accordance with one embodiment that may be used to carry out the methods described herein.

In some embodiments, the methods for calculating the effective dose to immune cells (EDIC) resulting from RT or a particular RT treatment plan are carried out on one or more suitably programmed computers. In some aspects, methods for calculating the EDIC and optimizing an RT treatment plan based on the calculated EDIC are carried out on a radiotherapy system. FIG. 5 illustrates a radiotherapy system 500 formed in accordance with an embodiment that can be used to carry out the methods disclosed and described herein. For example, the system 500 can be used to carry out the methods, including methods 100 (FIG. 1), 200 (FIG. 2), 300 (FIG. 3), and 400 (FIG. 4). In some embodiments, the methods can be automated by the system 500. In some embodiments, certain steps of the methods can be automated by the system 500 while others may be performed manually or otherwise require user interaction. In some embodiments, the user provides an initial treatment plan for a patient to the system 500, or otherwise causes an initial treatment plan to be provided to the system 500, and the system 500 automatically calculates the EDIC for the provided initial RT treatment plan and optimizes the initial RT treatment plan according to the methods described herein in accordance with pre-selected treatment criteria (e.g., reducing EDIC, or maximizing radiation dose to a tumor while minimizing EDIC to a predetermined range). In some embodiments, radiotherapy system 500 is an integrated standalone system that is located at one site. In other embodiments, one or more components of the system are located remotely with respect to each other. For example, in some embodiments, the EDIC calculator 510, treatment plan optimizer 512, database(s) 514, and storage system 518 may be implemented in multiple instances, distributed across multiple computing devices, instantiated within multiple virtual machines, and the like.

As depicted, the radiotherapy system 500 comprises a radiotherapy device 502; a treatment controller 504 comprising a user interface 506, a radiotherapy device controller 508, an EDIC calculator, and a treatment plan optimizer; one or more databases 514; one or more input/output (I/O) devices 516, and a storage system 518. In some embodiments, the database 514 provides past or proposed (i.e., initial) RT treatment plans and/or patient records to the treatment controller 504.

FIG. 5 provides a block diagram of a treatment controller 504 according to one embodiment. In some embodiments, the treatment controller 504 can calculate the EDIC for a provided RT treatment plan and/or control a radiotherapy device according to an optimized RT treatment plan. In some embodiments, the treatment controller 504 comprises a system controller 520, a user interface 506, a radiotherapy (RT) device controller 508, an EDIC calculator 510, and a treatment plan optimizer 512. The system controller 520 is communicatively coupled to the user interface 512 and/or the radiotherapy device 502. In some embodiments, the system control 520 comprises one or more processors/modules to calculate EDICs for particular treatment plans and, optionally, optimize the treatment plans in accordance with the methods described herein. For example, in some embodiments, the system control 520 includes one or more modules, each module being configured to execute a set of instructions that are stored in one or more storage elements (e.g., instructions stored on a tangible and/or non-transitory computer readable storage medium) to calculate EDICs and, optionally, optimize the treatment plan. In some embodiments the set of instructions includes various commands that instruct the system controller 520 as a processing machine to perform specific operations such as the processes and methods described herein.

As illustrated, the treatment controller 504 comprises a plurality of modules or submodules that control operation of the system controller 520. In some embodiments, the treatment controller 504 includes modules 508, 510, and 512, which are connected to or form a part of the system controller 520, and are connected to a storage system 518 and one or more databases 514. The storage system 518 and databases 514 can communicate with at least some of the modules 508, 510, 512, and system controller 520. In some embodiments, the modules comprise a radiotherapy device controller 508, an EDIC calculator 510, and a treatment plan optimizer 512. In some embodiments, the radiotherapy system 500 comprises additional modules or sub-modules, configures to perform the operations and methods described herein.

The EDIC calculator 510 is configured to receive an initial RT treatment plan, and optionally patient-specific anatomical information, from the database 514 or from the I/O device 516, and to calculate the EDIC from the RT treatment plan and optional patient-specific anatomical information according to the methods described herein.

The treatment plan optimizer 512 is configured to optimize a treatment plan, or otherwise select a treatment plan, according to the methods described herein.

The radiotherapy device controller 508 is configured to receive an optimized or otherwise selected treatment plan from treatment plan optimizer 512, and to control radiotherapy device 502. The radiotherapy device controller 508 is configured to cause the radiotherapy device 502 to administer a radiotherapy according to an optimized or otherwise selected radiotherapy treatment plan.

By way of example, the treatment controller 504 can be or include a desktop computer, a laptop computer, a notebook computer, a tablet computer, a smart phone, and the like. In some embodiments, the user interface 506 includes hardware, firmware, software, or a combination thereof that enables a user to directly or indirectly control operation of the system controller 520 and the various other modules and/or sub-modules. In some embodiments, the radiotherapy system 500 comprises an input/output (I/O) device 514, such as a keyboard, display printer, disk drive, universal serial bus (USB) port, a speaker, pointer device, trackball, button, switch, touch screen, and the like.

In some embodiments, the radiotherapy system 500 displays the initial RT treatment plan and the resulting optimized or selected RT treatment plan on an I/O device 516 that is a display. In other embodiments, the radiotherapy system 500 is configured to deliver a selected or optimized RT treatment plan to a printer, and email address, or other output.

In some embodiments, the radiotherapy system 500 comprises only those components necessary to select or optimize an RT treatment plan. For example, in some embodiments, the radiotherapy device 502 and the radiotherapy device controller 508 are excluded. Thus, in some embodiments, a radiotherapy treatment controller is provided. The radiotherapy treatment controller can be the same as the treatment controller 504 described above.

In some embodiments, a radiotherapy system 500 also includes one or more imaging modalities suitable for acquiring images of areas of interest, such as a target irradiation area within a patient. Suitable imaging modalities include, for example, computed tomography (CT) scanners, positron emission tomography (PET) scanners, magnetic resonance (MR) scanners, single photon emission computed tomography (SPECT) scanners, and the like. In some embodiments, the images acquired by the imaging modalities are three-dimensional images. In other embodiments, the images are two-dimensional. In certain embodiments, three-dimensional images include a stack of two dimensional images (i.e., slices). In some embodiments, the one or more imaging modalities are configured to provide patient-specific anatomical information to the treatment controller 504 or one of its components (e.g., EDIC calculator 510).

As used herein, the terms "module," "system," and "system controller" can refer to a hardware and/or software system and circuitry that operates to perform one or more functions. A module, system, or system controller may include a computer processor, controller, or other logic-based device that performs operations based on instructions stored on a tangible and non-transitory computer readable storage medium, such as a computer memory. Alternatively, a module, system, or system controller can include a hard-wired device that performs operations based on hard-wired logic and circuitry. The module, system, or system controller depicted in FIG. 5 can represent the hardware and circuitry that operates based on software or hardwired instructions, the software that directs hardware to perform the operations, or a combination thereof. The module, system, or system controller can include or represent hardware circuits or circuitry that include and/or are connected with one or more processors, such as one or more computer microprocessors.

As used herein, the terms "software" and "firmware" are interchangeable, and include any computer program stored in memory for execution by a computer, including Random Access Memory (RAM), Read Only Memory (ROM), Electronically Erasable Programmable Read Only Memory (EEPROM), non-volatile RAM (NVRAM), flash memory, optical or holographic media, magnetic cassettes, magnetic tape, magnetic disk storage or other magnetic storage devices, data transmissions, or any other medium that can be used to store information and can be accessed by a computing device. The above memory types are representative only, and are thus not limiting as to the types of memory usable for storage of a computer program.

In some embodiments, a processing unit, processor, module, or computing system that is "configured to" perform a task or operation can be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). A general purpose computer (which may become "configured to" perform the task or operation if appropriately programmed) is not "configured to" perform a task or operation unless or until specifically programmed or structurally modified to perform the task or operation.

In some embodiments, the memory stores computer-executable instructions for causing the system controller 520 to implement aspects of embodiments of system components discussed herein and/or to perform aspects of embodiments of methods and procedures discussed herein. Computer-executable instructions may include, for example, computer code, machine-useable instructions, and the like such as, for example, program components capable of being executed by one or more processors associated with a computing device. Program components may be programmed using any number of different programming environments, including various languages, development kits, frameworks, and/or the like. Some or all of the functionality contemplated herein may also, or alternatively, be implemented in hardware and/or firmware.

In some embodiments, elements of the radiotherapy system 500, such as the treatment controller 504 and modules or sub-modules thereof, database(s) 514, I/O device(s) 516, storage system 518, and radiotherapy device 502 are communicatively coupled by one or more communication links. In some embodiments, the one or more communication links can be, or include, a wired communication link such as a USB link, a proprietary wired protocol, and the like. The one or more communication links can be, or include, a wireless communication link such as a short-range radio link, such as Bluetooth IEEE 802.11, a proprietary wireless protocol, and the like.

The term "communication link" can refer to an ability to communicate some type of information in at least one direction between at least two elements of a computer system, and should not be understood to be limited to a direct, persistent, or otherwise limited communication channel. That is, according to some embodiments, the communication link may be a persistent communication link, an intermittent communication link, an ad-hoc communication link, and the like. The communication link can refer to direct communications or indirect communications between the radiotherapy device controller 508 and the radiotherapy device 502, between the database(s) 514 and the EDIC calculator, between the user interface 506 and the treatment plan optimizer 512, or any other combination of the elements of the radiotherapy system 500, wherein the indirect communication occurs via at least one other device (e.g., a repeater, router, hub, and/or the like). The communication link can facilitate unidirectional and/or bi-directional communication between the various elements of the radiotherapy system 500. In some embodiments, the communication link is, includes, or is included in a wired network, a wireless network, or a combination of wired and wireless networks. Illustrative networks include any number of different types of communication networks such as, a short messaging service (SMS), a local area network (LAN), a wireless LAN (WLAN), a wide area network (WAN), the Internet, a peer-to-peer (P2P) network, or other suitable networks. The network may include a combination of multiple networks. In some embodiments, for example, the radiotherapy system is accessible via the Internet (e.g., the radiotherapy system may facilitate a web-based RT treatment plan optimization/selection service), and a user may transmit one or more possible RT treatment plans to the radiotherapy system to optimize/select an adjusted RT treatment plan (i.e., a patient-specific radiotherapy treatment plan).

In some embodiments, the system controller 520 causes the EDIC calculator to access the database 514 and/or I/O device 516 to obtain one or more initial RT treatment plans via a communication link. Intermediary RT treatment plan data from the database(s) 514 can be web-based, cloud based, or local. In some embodiments the initial RT treatment plan data and/or the databases 514 are retrieved from a third party, produced by the user, or some combination thereof. The databases 514 can be any collection of information providing, for example, information regarding common RT treatment plans, patient data, and the like.

The following statements further describe various embodiments of the disclosure.

Statement 1. A radiotherapy system comprising a radiotherapy device configured to deliver a radiotherapy to a patient and a treatment controller having one or more processors and a non-transitory, tangible storage medium containing instructions that, when executed, cause the one or more processors to:
calculate from an initial radiotherapy treatment plan for a patient, an equivalent uniform dose (EUD) for each organ in a target irradiation area in the patient; calculate an effective dose of radiation to circulating immune cells in blood (EDIC) for the patient by summing all EUDs for all organs in the target irradiation area; and generate a new patient-specific radiotherapy treatment plan for the patient, wherein the new patient-specific radiotherapy treatment plan decreases a calculated EDIC relative to the initial radiotherapy treatment plan,
wherein the radiotherapy device is configured to deliver radiotherapy to the patient according to the new patient-specific radiotherapy treatment plan.

Statement 2. The radiotherapy system of statement 1, wherein the new patient-specific radiotherapy treatment plan further maximizes a radiation dose to a tumor.

Statement 3. The radiotherapy system of statement 1 or statement 2, wherein the new patient-specific radiotherapy treatment plan results in a calculated EDIC of 6.0 Gy or less.

Statement 4. The radiotherapy system of any one of statements 1-4, wherein the new patient-specific radiotherapy treatment plan is generated by adjusting the initial radiotherapy treatment plan by one or more of:
incorporating a hypofractionated radiotherapy treatment regimen;
decreasing radiation delivery time;
adjusting at least one of: beam energies, beam directions, and number of beams;
optimizing collimator margins;
incorporating an intensity-modulated radiotherapy planning technique;
incorporating an image-guided adaptive therapy technique;
incorporating a proton therapy technique;
dose de-escalation; and
margin reduction.

Statement 5. The radiotherapy system of any one of statements 1-4, wherein the new patient-specific radiotherapy treatment plan is generated by adjusting the initial radiotherapy treatment plan by one or more of:
increasing radiation delivery time;
adjusting at least one of: beam energies, beam directions, and number of beams;
optimizing collimator margins;
dose escalation; and
increasing margins.

Statement 6. The radiotherapy system of any one of statements 1-5, wherein the EUD for each organ is calculated from a dose volume histogram (DVH) for blood circulating through the organ, wherein the DVH after an ith radiation fraction represents a percentage of total body blood volume that receives a particular radiation dose when in the organ during the radiation fractions.

Statement 7. The radiotherapy system of any one of statements 1-5, wherein the EUD for each organ is calculated as a product of a percentage of blood volume B % in an organ, a mean organ dose for the organ, a dose effectiveness factor, and one half a quotient of n and a radiation saturation fraction factor, wherein n is a number of radiation fractions to be administered.

Statement 8. The radiotherapy system of any one of statements 1-5, wherein the EUD for each organ is calculated as a product of a percentage of blood volume B % in an organ and a mean organ dose for the organ, wherein B % is an amount of blood contained in the organ at any time relative to a total body blood volume, a number of radiation fractions to be administered to the patient is equal to or greater than a quotient of a radiation saturation fraction factor and V %, wherein V % is a percentage of blood that receives a radiation dose as the blood passes through the organ.

Statement 9. The radiotherapy system of any one of the statements herein, wherein the target irradiation area is a thoracic area, and the EDIC is calculated by summing the EUDs for the patient's lungs, heart, thoracic great vessels, and small vessels and capillaries in the thoracic area. The DVH of small vessels and capillaries can be represented by the DVH of the total body.

Statement 10. The radiotherapy system of any one of the statements herein, further comprising one or more imaging modalities.

Statement 11. The radiotherapy system of any one of the statements herein, wherein the instructions, when executed, cause the one or more processors to generate one or more additional new patient-specific radiotherapy treatment plans for the patient during delivery of the new patient-specific radiotherapy treatment plan to the patient.

Statement 12. A method for treating a patient, the method comprising:
calculating from an initial radiotherapy treatment plan for the patient, an equivalent uniform dose (EUD) for each organ in a target irradiation area in the patient;
calculating an effective dose of radiation to circulating immune cells in blood (EDIC) for the patient by summing all EUDs for all organs in the target irradiation area;
generating a new patient-specific radiotherapy treatment plan for the patient, wherein the new patient-specific radiotherapy treatment plan decreases a calculated EDIC relative to the initial radiotherapy treatment plan; and
delivering radiotherapy to the patient according to the new patient-specific radiotherapy treatment plan.

Statement 13. The method of statement 12, wherein the new patient-specific radiotherapy treatment plan further maximizes a radiation dose to a tumor.

Statement 14. The method of statement 12 or statement 13, wherein the new patient-specific radiotherapy treatment plan results in a calculated EDIC of 6.0 Gy or less.

Statement 15. The method of any one of statements 12-14, wherein the new patient-specific radiotherapy treatment plan is generated by adjusting the initial radiotherapy treatment plan by one or more of:
incorporating a hypofractionated radiotherapy treatment regimen;
decreasing radiation delivery time;
adjusting at least one of: beam energies, beam directions, and number of beams;

optimizing collimator margins;
incorporating an intensity-modulated radiotherapy planning technique;
incorporating an image-guided adaptive therapy technique;
incorporating a proton therapy technique;
dose de-escalation; and
margin reduction.

Statement 16. The method of any one of statements 12-14, wherein the new patient-specific radiotherapy treatment plan is generated by amending the initial radiotherapy treatment plan by one or more of:
increasing radiation delivery time;
adjusting at least one of: beam energies, beam directions, and number of beams;
optimizing collimator margins;
dose escalation; and
increasing margins.

Statement 17. The method of any one of statements 12-16, wherein the EUD for each organ is calculated from a dose volume histogram (DVH) for blood circulating through the organ, wherein the DVH after an ith radiation fraction represents a percentage of total body blood volume that receives a particular radiation dose when in the organ during the radiation fractions.

Statement 18. The method of any one of statements 12-16, wherein the EUD for each organ is calculated as a product of a percentage of blood volume B % in an organ, a mean organ dose for the organ, a dose effectiveness factor, and one half a quotient of n and a radiation saturation fraction factor, wherein n is a number of radiation fractions to be administered.

Statement 19. The method of any one of statements 12-16, wherein the EUD for each organ is calculated as a product of a percentage of blood volume B % in an organ and a mean organ dose for the organ, wherein B % is an amount of blood contained in the organ at any time relative to a total body blood volume, a number of radiation fractions to be administered to the patient is equal to or greater than a quotient of a radiation saturation fraction factor and V %, wherein V % is a percentage of blood that receive a radiation dose as the blood passes through the organ.

Statement 20. The method of treatment of any one of the statements herein, wherein the target irradiation area is a thoracic area, and the EDIC is calculated by summing the EUDs for the patient's lungs, heart, thoracic great vessels, and small vessels and capillaries in the thoracic area.

Statement 21. The method of treatment of any one of the statements herein, further comprising acquiring an image of the target irradiation area in the patient utilizing at least one imaging modality.

Statement 22. The method of treatment of any one of the statements herein, further comprising generating one or more additional new patient-specific radiotherapy treatment plans for the patient during delivery of the new patient-specific radiotherapy treatment plan to the patient, stopping delivery of the new patient-specific radiotherapy treatment plan to the patient, and delivering one of the one or more additional new patient-specific radiotherapy treatment plans.

Statement 23. A radiotherapy system comprising a radiotherapy device configured to deliver a radiotherapy in accordance with a radiotherapy plan and one or more processors programmed to perform the two calculating steps and the generating step of the method according to any one of statements 12-16.

Statement 24. A non-transitory computer-readable medium having instructions stored thereon for causing one or more processors to perform the two calculating steps and the generating step of the method according to any one of statements 12-16.

Statement 25. A radiotherapy treatment controller comprising one or more processors and a non-transitory, tangible storage medium containing instructions that, when executed, cause the one or more processors to:
calculate from an initial radiotherapy treatment plan for a patient, an equivalent uniform dose (EUD) for each organ in a target irradiation area in the patient;
calculate an effective dose of radiation to circulating immune cells in blood (EDIC) for the patient by summing all EUDs for all organs in the target irradiation area; and
generate a new patient-specific radiotherapy treatment plan for the patient, wherein the new patient-specific radiotherapy treatment plan decreases a calculated EDIC relative to the initial radiotherapy treatment plan.

Statement 26. The radiotherapy treatment controller of statement 25, wherein the radiotherapy treatment controller is communicatively coupled to a radiotherapy device configured to deliver radiotherapy to the patient.

Statement 27. The radiotherapy treatment controller of statement 25 or statement 26, wherein the radiotherapy device is configured to deliver the radiotherapy to the patient according to the new patient-specific radiotherapy treatment plan.

Statement 28. The radiotherapy treatment controller of any one of statements 25-27, wherein the new patient-specific radiotherapy treatment plan further maximizes a radiation dose to a tumor.

Statement 29. The radiotherapy treatment controller of any one of statements 25-28, wherein the new patient-specific radiotherapy treatment plan results in a calculated EDIC of 6.0 Gy or less.

Statement 30. The radiotherapy treatment controller of any one of statements 25-29, wherein the new patient-specific radiotherapy treatment plan is generated by adjusting the initial radiotherapy treatment plan by one or more of:
incorporating a hypofractionated radiotherapy treatment regimen;
decreasing radiation delivery time;
adjusting at least one of: beam energies, beam directions, and number of beams;
optimizing collimator margins;
incorporating an intensity-modulated radiotherapy planning technique;
incorporating an image-guided adaptive therapy technique;
incorporating a proton therapy technique;
dose de-escalation; and
margin reduction.

Statement 31. The radiotherapy treatment controller of any one of statements 25-29, wherein the new patient-specific radiotherapy treatment plan is generated by adjusting the initial radiotherapy treatment plan by one or more of:
increasing radiation delivery time;
adjusting at least one of: beam energies, beam directions, and number of beams;
optimizing collimator margins;
dose escalation; and
increasing margins.

Statement 32. The radiotherapy treatment controller of any one of statements 25-31, wherein the EUD for each organ is calculated from a dose volume histogram (DVH) for blood circulating through the organ, wherein the DVH after an ith radiation fraction represents a percentage of total body blood volume that receives a particular radiation dose when in the organ during the radiation fractions.

Statement 33. The radiotherapy treatment controller of any one of statements 25-31, wherein the EUD for each organ is calculated as a product of a percentage of blood volume B % in an organ, a mean organ dose for the organ, a dose effectiveness factor, and one half a quotient of n and a radiation saturation fraction factor, wherein n is a number of radiation fractions to be administered.

Statement 34. The radiotherapy treatment controller of any one of statements 25-31, wherein the EUD for each organ is calculated as a product of a percentage of blood volume B % in an organ and a mean organ dose for the organ, wherein B % is an amount of blood contained in the organ at any time relative to a total body blood volume, a number of radiation fractions to be administered to the patient is equal to or greater than a quotient of a radiation saturation fraction factor and V %, wherein V % is a percentage of blood that receives a radiation dose as the blood passes through the organ.

Statement 35. The radiotherapy treatment controller of any one of statements 25-34, wherein the target irradiation area is a thoracic area, and the EDIC is calculated by summing the EUDs for the patient's lungs, heart, thoracic great vessels, and small vessels and capillaries in the thoracic area.

EXAMPLES

The materials, methods, and embodiments described herein are further defined in the following Examples. Certain embodiments are defined in the Examples herein. It should be understood that these Examples, while indicating certain embodiments, are given by way of illustration only. From the disclosure herein and these Examples, one skilled in the art can ascertain the essential characteristics of this invention, and without departing from the spirit and scope thereof, can make various changes and modifications of the invention to adapt it to various usages and conditions.

Example 1—Higher Radiation Dose to Immune System Correlates with Poorer Survival in Patients With Stage III Non-Small Cell Lung Cancer In one example of the embodiments described herein, it is demonstrated that higher radiation doses to circulating immune cells results in poorer overall survival in patients with stage III non-small cell lung cancer.

Lung cancer is the leading cause of cancer-related death worldwide. Over 85% of lung cancers are non-small cell lung cancer (NSCLC), and 40% are stage III. Standard care for unresectable stage III NSCLC is radiotherapy (RT) with concurrent chemotherapy. Despite advances in RT technology, treatment outcome remains suboptimal, and local disease progression is a major cause of death. Intensifying local therapy with RT dose escalation was therefore believed to improve local tumor control and survival. RTOG 0617 was designed to test the effects of radiation dose escalation in locally advanced NSCLC and randomized patients to high-dose (74 Gy) versus low-dose (60 Gy) chemoradiation (Bradley et al., Lancet Oncol. 2015 Feb., 16(2):187-199). However, the results of the RTOG study unexpectedly revealed significantly worse overall survival (OS) with the high-dose regimen.

Recent reports suggest that radiation-induced tumor cell killing can activate the immune system by releasing tumor specific antigens. Preclinical studies have demonstrated that the immune system plays a key role in tumor control during RT. Treatments with RT alone or RT combined with immunotherapy controlled the tumors in immunocompetent mice, but not in immune-deficient mice. An abscopal effect (i.e., shrinkage of un-irradiated tumors far apart from the RT fields) has been observed in animal studies and in single-patient case report. While these observations suggest that RT may augment anti-tumor immunity in certain settings, RT is also well known to have immunosuppressive effects. One of the most common and clinically significant features of radiation-induced immunosuppression is radiation-induced lymphopenia, which has been repeatedly associated with poorer survival in several studies as well as in a recent pooled analysis of multiple treatment-refractory solid tumors.

In the study described in this example, it was hypothesized that excessive RT dose to the immune system impairs various immune functions including anti-tumor immunity and leads to decreasing patient disease control and survival. To test this hypothesis, a model was first developed to compute the effective dose to immune cells (EDIC) during the entire RT course, and the relationship between EDIC and the risk of tumor progression and death was evaluated. The RTOG 0617 trial provided a setting for testing this hypothesis, as detailed dosimetric and survival data were available for nearly all patients enrolled in this large phase III cooperative group trial.

Patient, Clinical Data, and Dosimetry Data

RTOG 0617 was a phase 3 trial for unresectable stage III NSCLC (Bradley et al., Lancet Oncol. 2015 Feb., 16(2): 187-199). All patients received conformal radiotherapy with concurrent and consolidation chemotherapy (carboplatin and paclitaxel). The treatment options of RT dose (60 Gy vs. 74 Gy) and cetuximab (yes vs. no) were used in the two-by-two factorial randomized design. All eligible patients who had retrievable RT plans and received at least 51 Gy were included in the present analysis. Clinical factors analyzed for survival and tumor control included baseline Zubrod performance status, use of positron emission tomography (PET) during staging, tumor histology, age at randomization, gender, race, tumor locations, weight loss, smoking history, gross tumor volume (GTV), and whether patients received full courses of chemotherapy. Conventional radiation dosimetry data such as mean lung dose (MLD), mean heart dose (MHD) and integral total dose (ITD) were also included for modeling.

EDIC Computation

The immune system has not generally been considered as an organ at risk for RT toxicity, and no guidelines presently exist to delineate the immune system for the purposes of RT planning. In this example and throughout the present disclosure, lymphocytes are considered as the main immune cell of interest, as lymphocytes are the primary effector cells in antitumor immunity. Furthermore, radiation-induced lymphopenia has been implicated as an important biomarker of worse outcomes in patients undergoing RT. Under normal conditions, lymphocytes originate in the bone marrow and/or thymus and circulate through the body via both blood vessels and lymphatic ducts. Lymphocytes are trafficked through the secondary lymphatic organs (spleen and lymph nodes), and migrate to tumor if an immune response is activated. It was also reported that irradiation of circulating blood is a mechanism for inducing lymphopenia because it occurs after irradiation of tissues such as the breast and brain that contain little marrow or lymphatic tissue. Therefore, the radiation dose to the blood was considered as a surrogate for EDIC, and it was demonstrated that EDIC can be simply estimated by equation 6 for patients receiving ≥25 fractions of thoracic radiation:

$$EDIC = B_1\% * MLD + B_2\% * MHD + \left[B_3\% + B_4\% * k_1 * \left(\frac{n}{45}\right)^{\frac{1}{2}}\right] * ITD/(61.8 * 10^3), \quad (6)$$

wherein B1%=0.12, B2%=0.08, B3%=0.45 and B4%=0.35 represent the percentage of blood volume within the four major blood-containing organs (lung, heart, great vessels, and small vessels/capillaries in all other organs) of the total blood volume in the body, respectively, k1=0.85 is a dose effectiveness factor for the small vessels/capillaries, and 61.8*103 (cm³) is the average total body volume, assuming average weight and density of 70 lps/63 kg and 1.02 g/cm³. A detailed derivation of this equation is provided in the present disclosure.

Outcomes and Statistical Considerations

Risks of death and progressive disease were quantified through overall survival (OS), progression-free survival (PFS) and local progression-free survival (LPFS). They were analyzed as time-to-event data and calculated from the date of randomization to the date of respective event or last follow-up. The OS event was death due to any cause; the PFS event was the first occurrence of any progression or death; the LPFS event was the first occurrence of local failure or death. These rates were estimated using the Kaplan-Meier method, and the distributions between different groups were compared using the log-rank test. Cox proportional hazards models were used to evaluate the relationship between EDIC and other factors with OS, PFS and LPFS. Because EDIC was derived from the combination of MLD, MHD and ITD, these variables were evaluated individually under multivariable analyses to avoid potential collinearity. The functional forms of EDIC in the Cox models were explored both linearly and using restricted cubic splines. To illustrate the non-linear functional form of EDIC in the Cox model, EDIC was also categorized based on quartiles and absolute EDIC values. The proportionality assumption was graphically assessed using plots of log(-log[survival]) versus log of survival time, and tested using a formal test based on the Schoenfeld residuals. Interaction terms (e.g., potentially differential effects of EDIC on outcomes by different levels of patient characteristics) were also examined using the Wald test.

Results

Patient Characteristics

Of 495 eligible patients enrolled in the RTOG 0617 study, 466 had retrievable RT plans. Ten patients were excluded from this analysis for the following reasons: RT plan missed the target (n=1), incorrectly archived RT plan (exactly same plan for 2 different patients) (n=4), or total dose received was ≤51 Gy (n=5). Of the 456 remaining patients, 256 and 200 were originally assigned to the standard (60 Gy) and high dose arms (74 Gy), respectively; 261 patients received 60 Gy (including 5 patients originally assigned to the high dose arm), 165 received 74 Gy, 4 received 52-58 Gy, 12 received 62-66 Gy, and 6 received 67-72 Gy. The patients were categorized according to the actual dose received, with a dose of >67 Gy defined as high dose. Based on this definition, 285 and 171 patients were placed into the low- and high-dose groups, respectively.

Median follow-up time for patients alive at the last evaluation was 30.3 months (range 2.5-61.5 months). Demographic, clinical, and dosimetric data are summarized in Table 2. EDIC was calculated for all 456 patients. Median EDIC was 5.58 Gy (range 2.05-12.20 Gy) for the low dose group, 6.34 Gy (2.14-11.59 Gy) for the high dose group, and 5.94 Gy (2.05-12.20 Gy) for all patients.

TABLE 2

Patient Characteristic and their difference between the two tumor dose groups. P <0.05 denotes that there is a significant difference between the two groups

| Characteristics | Dose <67 Gy (n = 285) | Dose ≥ 67 Gy (n = 171) | Total (n = 456) | p-Value |
|---|---|---|---|---|
| Age | 64 (37-82) | 64 (41-84) | 64 (37-84) | 0.89 |
| Gender | | | | 0.43 |
| Male | 174 (61%) | 98 (57%) | 272 (60%) | |
| Female | 111 (39%) | 73 (435) | 184 (40%) | |
| Race | | | | 0.44 |
| White | 242 (85%) | 152 (89%) | 394 (86%) | |
| Black | 31 (11%) | 13 (8%) | 44 (10%) | |
| Others | 12 (4%) | 6 (3%) | 18 (4%) | |
| Zubrod | | | | 0.90 |
| 0 | 170 (60%) | 101 (59%) | 271 (59%) | |
| 1 | 115 (40%) | 70 (41%) | 185 (41%) | |
| Histology | | | | 0.68 |
| Squamous | 122 (43%) | 73 (43%) | 195 (43%) | |
| Adeno | 114 (40%) | 65 (38%) | 179 (39%) | |
| Others | 48 (17%) | 33 (19%) | 81 (18%) | |
| AJCC Stage | | | | 0.73 |
| IIIa | 190 (67%) | 111 (65%) | 301 (66%) | |
| IIIb | 94 (33%) | 59 (35%) | 153 (34%) | |
| RT Technique | | | | 0.48 |
| 3D-CRT | 153 (54%) | 86 (50%) | 239 (52%) | |
| IMRT | 132 (46%) | 85 (50%) | 217 (48%) | |

TABLE 2-continued

Patient Characteristic and their difference between the two tumor dose groups. P <0.05 denotes that there is a significant difference between the two groups

| Characteristics | Dose <67 Gy (n = 285) | Dose ≥ 67 Gy (n = 171) | Total (n = 456) | p-Value |
|---|---|---|---|---|
| PET Staging | | | | 0.37 |
| No | 23 (8%) | 18 (11%) | 41 (9%) | |
| Yes | 262 (92%) | 153 (90%) | 415 (91%) | |
| Tumor Location | | | | 0.48 |
| LLL/central location | 32 (11%) | 23 (14%) | 55 (12%) | |
| Others | 253 (89%) | 148 (87%) | 401 (88%) | |
| Weight loss/month | 0 (0-9%) | 0 (0-7%) | 0 (0-9%) | 0.99 |
| Esophagitis Grade | | | | 0.03 |
| Grade < 3 | 253 (89%) | 139 (81%) | 392 (86%) | |
| Grade ≥ 3 | 32 (11%) | 32 (19%) | 64 (14%) | |
| Received full Chemo | | | | 0.095 |
| No | 42 (15%) | 16 (9%) | 58 (13%) | |
| Yes | 243 (85%) | 155 (91%) | 398 (87%) | |
| GTV (cc) | 92.7 (4.6-960.7) | 93.7 (5.4-698.9) | 92.7 (4.6-961) | 0.48 |
| MLD (Gy) | 17.4 (5.4-31.7) | 20.1 (5.1-32.7) | 18.4 (5.1-32.7) | <0.0001 |
| MHD (Gy) | 13.2 (0-47.1) | 12.6 (0.4-49.4) | 12.7 (0-49.4) | 0.45 |
| ITD (Gy•liter) | 206 (62-545) | 244 (104-464) | 218 (62-545) | <0.0001 |
| EDIC (Gy) | 5.58 (2.05-12.20) | 6.34 (2.14-11.59) | 5.94 (2.05-12.2) | <0.0001 |

Abbreviations: RT: Radiotherapy; 3D-CRT: 3-D conformal radiation therapy; IMRT: intensity modulated radiation therapy; LLL: low left lobe; GTV: gross tumor volume; MLD: mean lung dose; MHD: mean heart dose; ITD: integral total dose; EDIC: effective dose to the immune cells; OS: overall survival; PFS: Progression free survival; LPFS: Local regional progression free survival.

Univariate Analysis for OS, PFS, and LPFS

When patients were re-categorized according to the dose actually received, the low-dose patients had marginally better OS and PFS, and significantly better LPFS than the high-dose patients. This tumor dose effect was adjusted by stratifying it in the univariate analysis for all other potential prognostic factors. Gender, Zubrod performance status, tumor histology, smoking history, use of PET staging, AJCC stage were not significantly associated with OS, PFS and LPFS, while the occurrence of grade ≥3 esophagitis/dysphagia and completion of full course of chemotherapy were significantly associated with OS, PFS and LPFS (Table 3). Tumor location (central/lower left lobe vs. others) was significantly associated with OS only. All dosimetric factors, including GTV, MLD, MHD, ITD and EDIC, were significantly associated with OS, PFS and LPFS, except ITD, which was only significantly associated with OS (Table 3).

TABLE 3

Univariate analysis stratified by actually received dose*

| | OS | | PFS | | LPFS | |
|---|---|---|---|---|---|---|
| Variables | HR (95% CI) | p value | HR (95% CI) | p value | HR (95% CI) | p value |
| Prescription dose | 1.31 (1.04, 1.67) | 0.01 | 1.22 (0.98, 1.51) | 0.07 | 1.34 (1.07-1.67) | 0.01 |
| Actual received dose | 1.22 (0.95, 1.56) | 0.10 | 1.21 (0.98, 1.50) | 0.08 | 1.32 (1.05, 1.65) | 0.017 |
| Age | 1.01 (0.99, 1.02) | 0.24 | 0.997 (0.99, 1.009) | 0.59 | 1.01 (0.99, 1.02) | 0.26 |
| Gender | 0.83 (0.65, 1.06) | 0.13 | 0.96 (0.77, 1.19) | 0.71 | 0.88 (0.70, 1.10) | 0.27 |
| Zubrod | 1.02 (0.80, 1.30) | 0.86 | 0.95 (0.76, 1.18) | 0.64 | 1.01 (0.81, 1.27) | 0.91 |
| Histology | 1.13 (0.88, 1.43) | 0.34 | 1.02 (0.82, 1.26) | 0.87 | 1.19 (0.95, 1.49) | 0.12 |
| Smoke History | 0.72 (0.43, 1.21) | 0.22 | 0.79 (0.50, 1.26) | 0.32 | 0.80 (0.50, 1.30) | 0.37 |
| RT Technique | 0.89 (0.70, 1.13) | 0.33 | 1.04 (0.84, 1.28) | 0.74 | 1.06 (0.84, 1.32) | 0.64 |
| PET Staging | 0.76 (0.52, 1.11) | 0.16 | 0.87 (0.61, 1.24) | 0.45 | 0.83 (0.58, 1.21) | 0.34 |
| AJCC Stage | 1.03 (0.80, 1.32) | 0.82 | 1.08 (0.86, 1.35) | 0.52 | 1.08 (0.86, 1.37) | 0.49 |
| Tumor Location | 1.49 (1.06, 2.09) | 0.02 | 1.21 (0.88, 1.66) | 0.25 | 1.33 (0.95, 1.84) | 0.09 |
| Esophagitis grade | 1.77 (1.30, 2.41) | 0.0003 | 1.72 (1.29, 2.28) | 0.0002 | 1.53 (1/14. 2.06) | 0.005 |
| Received full Chemo | 0.64 (0.46, 0.90) | 0.009 | 0.72 (0.53, 0.97) | 0.03 | 0.70 (0.51, 0.97) | 0.03 |

TABLE 3-continued

Univariate analysis stratified by actually received dose*

| Variables | OS HR (95% CI) | p value | PFS HR (95% CI) | p value | LPFS HR (95% CI) | p value |
|---|---|---|---|---|---|---|
| GTV | 1.21 (1.07, 1.38) | 0.0026 | 1.13 (1.01, 1.26) | 0.03 | 1.13 (1.01, 1.27) | 0.04 |
| Mean Lung Dose | 1.05 (1.02, 1.09) | 0.0004 | 1.04 (1.01, 1.07) | 0.003 | 1.03 (1.004, 1.06) | 0.02 |
| Mean Heart Dose | 1.02 (1.01, 1.03) | <0.0001 | 1.01 (1.003, 1.02) | 0.004 | 1.02 (1.007, 1.03) | 0.0007 |
| Total Body Dose | 1.003 (1.001, 1.005) | 0.0004 | 1.001 (1.00, 1.003) | 0.11 | 1.002 (1.00, 1.003) | 0.03 |
| EDIC | 1.18 (1.10, 1.26) | <0.0001 | 1.10 (1.03, 1.16) | 0.002 | 1.11 (1.05, 1.18) | 0.0009 |

*The effect of actual received dose has been stratified for all other factors in this univariate analysis except for the prescription dose and actually received dose.
Abbreviations:
RT: Radiotherapy;
HR: Hazard ratio;
CI: confident interval;
GTV: gross tumor volume;
EDIC: effective dose to the immune cells;
OS: overall survival;
PFS: Progression free survival;
LPFS: Local regional progression free survival.

Multivariate Analysis for OS, PFS, and LPFS

The clinical and dosimetric factors that were identified of interest from univariate analysis were further studied using stratified multivariable analyses according to the actual RT dose received for OS, PFS and LPFS in two different multivariate models: one without EDIC but with MLD/MHD/ITD, and one with EDIC but without MLD/MHD/ITD. The occurrence of grade ≥3 esophagitis/dysphagia and completion of chemotherapy remained significantly associated with OS, PFS and LPFS for both models (Tables 4a-4c). In the OS model without EDIC, the MHD, MHD and ITD were no longer significant factors, and GTV remained significant. While in the model with EDIC, EDIC was significantly associated with OS but the GTV was not (Table 4a). MLD and GTV were significantly associated with PFS (Table 4b), while MHD was significantly associated with LPFS (Table 4c) in the multivariable models without EDIC. While EDIC was not significantly associated with PFS, it was significantly associated with LPFS in the multivariable models (Tables 4b and 4c).

Tables 4a-4c. Stratified multivariable analyses according to the actual received RT dose.

TABLE 4a

| Variables | OS Without EDIC HR (95% CI) | p-Value | OS With EDIC HR (95% CI) | p-Value |
|---|---|---|---|---|
| Tumor Location | 1.42 (0.98, 2.05) | 0.07 | 1.41 (0.98, 2.02) | 0.07 |
| Gross tumor volume | 1.16 (1.00, 1.34) | 0.05 | 1.12 (0.98, 1.28) | 0.09 |
| Esophagitis grade | 1.53 (1.11, 2.11) | 0.01 | 1.52 (1.10, 2.10) | 0.012 |
| Received full Chemo | 0.58 (0.41, 0.81) | 0.0015 | 0.59 (0.42, 0.83) | 0.003 |
| Mean lung dose | 1.03 (0.998, 1.070) | 0.07 | | |
| Mean heart dose | 1.008 (0.995, 1.022) | 0.21 | | |
| Integral total dose | 1.000 (0.998, 1.002) | 0.93 | | |
| EDIC | | | 1.12 (1.03, 1.21) | 0.005 |

TABLE 4b

| Variables | PFS Without EDIC HR (95% CI) | p-Value | PFS With EDIC HR (95% CI) | p-Value |
|---|---|---|---|---|
| Tumor Location | 1.19 (0.84, 1.68) | 0.33 | 1.20 (0.85, 1.68) | 0.30 |
| Gross tumor volume | 1.15 (1.01, 1.32) | 0.04 | 1.08 (0.96, 1.21) | 0.20 |
| Esophagitis grade | 1.64 (1.22, 2.21) | 0.001 | 1.60 (1.19, 2.15) | 0.002 |
| Received full Chemo | 0.63 (0.46, 0.86) | 0.003 | 0.66 (0.49, 0.90) | 0.009 |
| Mean lung dose | 1.04 (1.006, 1.071) | 0.02 | | |
| Mean heart dose | 1.005 (0.992, 1.017) | 0.47 | | |
| Integral total dose | 0.998 (0.996, 1.000) | 0.10 | | |
| EDIC | | | 1.05 (0.98, 1.12) | 0.17 |

TABLE 4c

| Variables | LPFS Without EDIC | | LPFS With EDIC | |
|---|---|---|---|---|
| | HR (95% CI) | p-Value | HR (95% CI) | p-Value |
| Gross tumor volume | 1.09 (0.97, 1.23) | 0.13 | 1.07 (0.95, 1.20) | 0.29 |
| Esophagitis grade | 1.36 (1.00, 1.85) | 0.05 | 1.37 (1.00, 1.86) | 0.05 |
| Received full Chemo | 0.66 (0.48, 0.91) | 0.012 | 0.67 (0.48, 0.92) | 0.013 |
| Mean lung dose | 1.01 (0.98, 1.04) | 0.51 | | |
| Mean heart dose | 1.012 (1.000, 1.024) | 0.045 | | |
| EDIC | | | 1.09 (1.01, 1.16) | 0.02 |

Abbreviations: HR: Hazard ratio; CI: confident interval; EDIC: effective dose to the immune cells; OS: overall survival; PFS: Progression free survival; LPFS: Local regional progression free survival.

Relationship Between EDIC and OS

Figure 6A:
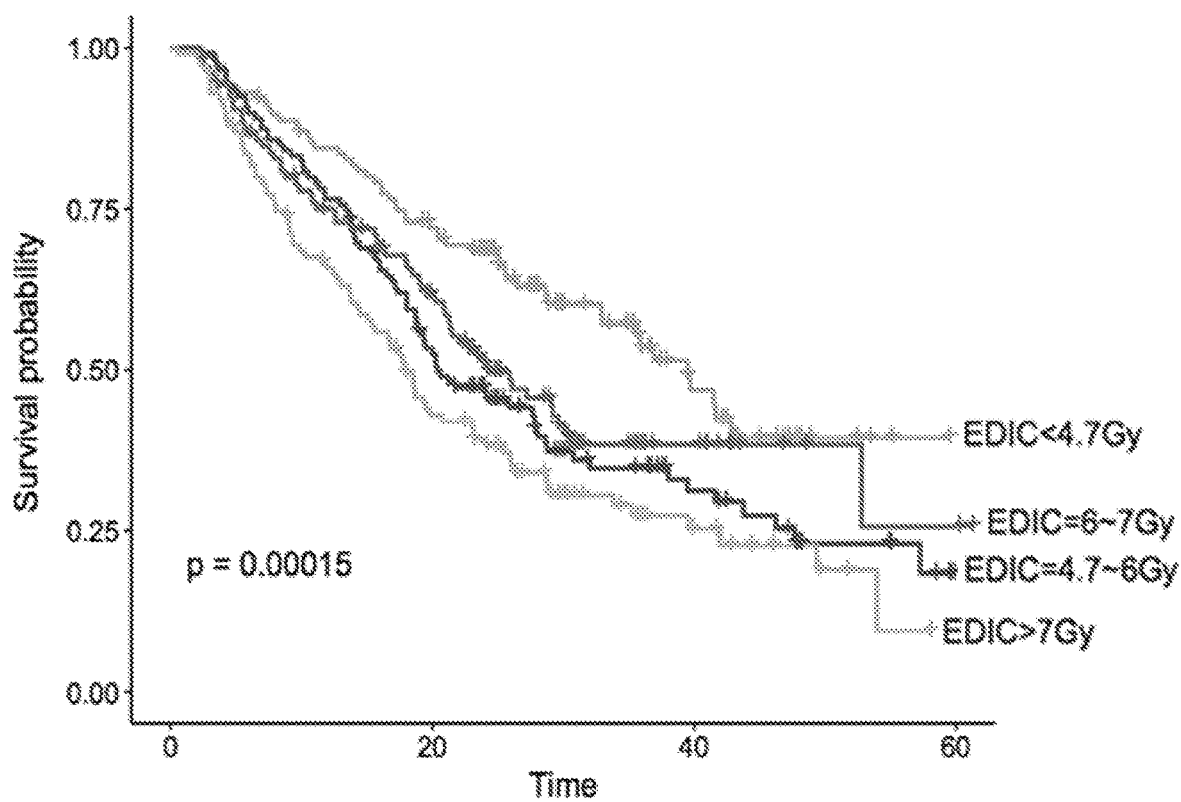
FIG. 6A depicts overall survival curves for patients divided into four quartiles according to the effective radiation dose to circulating immune cells (EDIC), in accordance with embodiments of the disclosure.
Figure 6B:
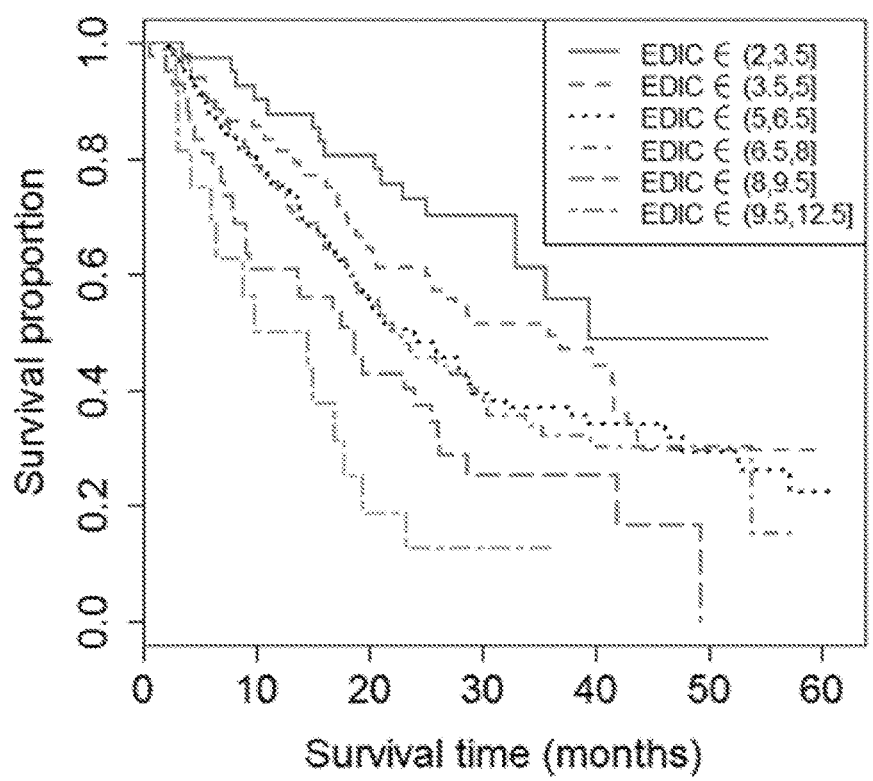
FIG. 6B depicts overall survival curves for patients divided into six EDIC groups according to absolute EDIC values with a 1.5-Gy dose-increment, in accordance with embodiments of the disclosure.
Figure 7A:
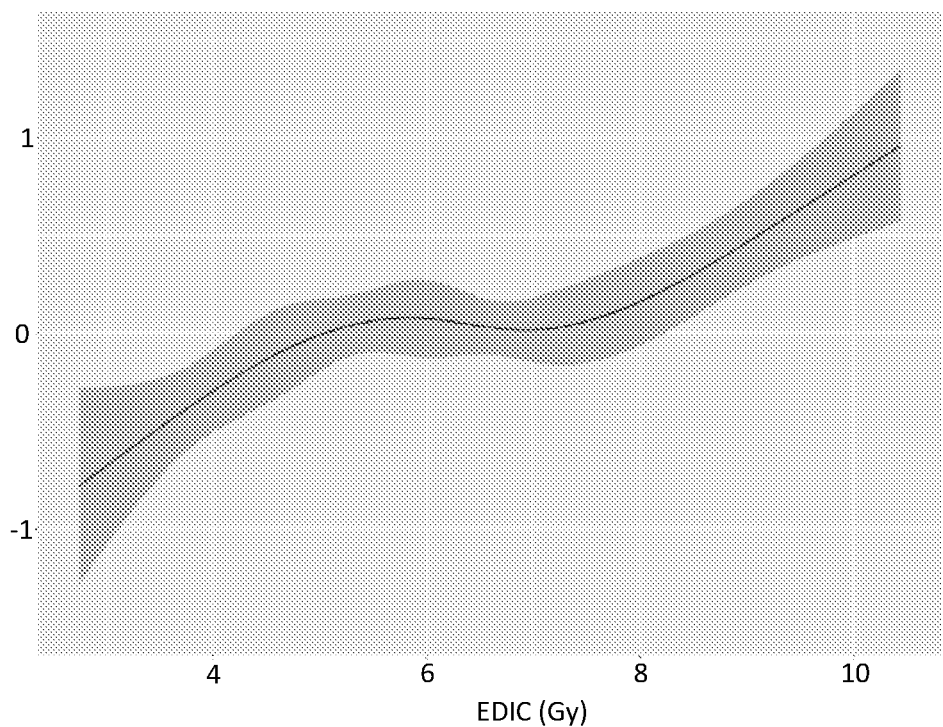
FIG. 7A depicts the relationship between relative hazard of death and EDIC, in accordance with embodiments of the disclosure.

To further analyze the relationship between EDIC and OS, patients were divided into four quartiles according to EDIC (FIG. 6A) as well as into six groups based on absolute EDIC (using 1.5-Gy increments; FIG. 6B). The Kaplan-Meier curves shown in FIG. 6 depict a strong inverse relationship between OS and EDIC (i.e., as EDIC increases, OS decreases). However, the relationship between EDIC and OS is non-linear, as shown in the hazard-versus-EDIC curve created through nonparametric smoothing using restricted cubic splines (FIG. 7A). This analysis shows that hazard rates increase with increasing EDIC when EDIC is less than 6.0 Gy or larger than 8.0 Gy. Univariate Cox models with stratified tumor dose demonstrated that death hazard increased by 23%/Gy (1.07, 1.41), p=0.003 with increasing EDIC when EDIC<6.0, and by 37%/Gy (1.14, 1.64), p=0.0007 when EDIC>8 Gy. However, this curve is relatively flat when EDIC is between 6.0-8.0 Gy.

Figure 7B:
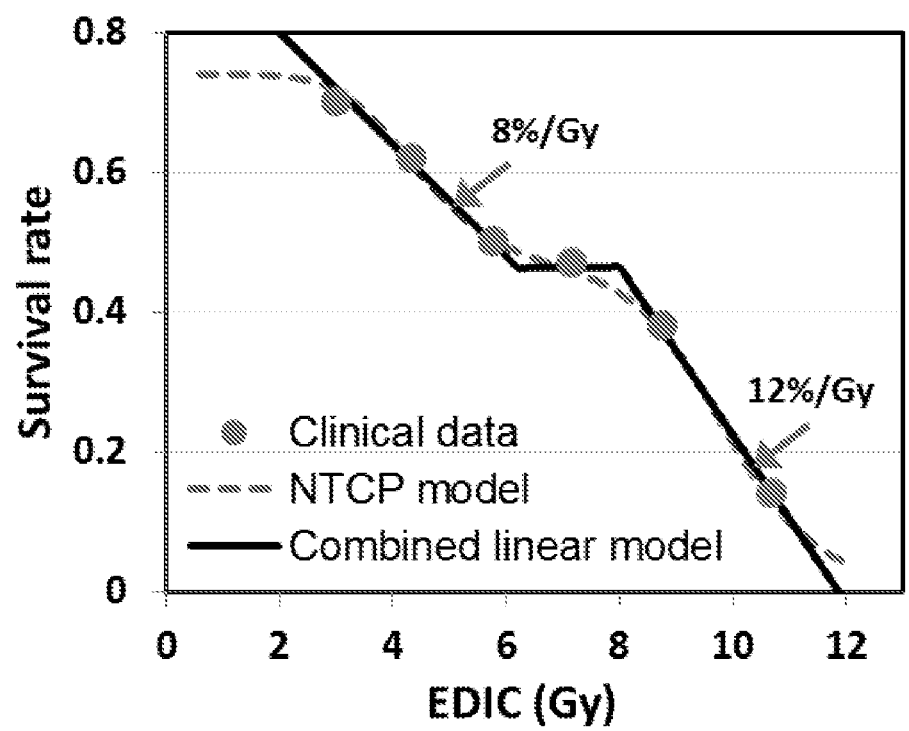
FIG. 7B depicts the relationship between two-year overall survival rate and EDIC by normal tissue complication probability (NTCP) survival mode, in accordance with embodiments of the disclosure.

This non-linear relationship is also illustrated by the survival-dose response curve for 2-year OS versus EDIC (FIG. 7B). The 6 data points were determined from the data of 6 subgroups in FIG. 6B, with the horizontal axis of each point being the average EDIC for the corresponding subgroup. The data are well fitted by an OS model composed of two normal tissue complication probability (NTCP) components:

$$OS = 0.74 * \left[1 - \frac{0.39}{1 + \left(\frac{4.5}{EDIC}\right)^6}\right] * \left[1 - \frac{1}{1 + \left(\frac{9.9}{EDIC}\right)^{12}}\right]$$

with $D_{50}$ being 4.5 and 9.9 Gy, respectively, for the two NTCP components, suggesting two responding mechanisms or structures for the relationship. Alternatively, the survival-dose response can also be simply described by a combined linear model with 3 parts: 1) EDIC <6.0 Gy, 2-year OS decreases with increasing EDIC at a slope of 8%/Gy; 2) EDIC between 6.0-8.0 Gy, OS keeps flat; 3) EDIC>8.0 Gy, 2-year OS decreases with increasing EDIC at a slope of 12%/Gy.

A direct clinical implication of this study is that circulating immune cells should be considered as a critical organ at risk and that EDIC should be limited in routine clinical practice. The data suggest that patients with either high (>8.0 Gy) or low EDIC (<6.0 Gy) can benefit from this finding. Patients at the high EDIC levels would be expected to derive the largest benefit (12% expected OS improvement with a 1-Gy EDIC reduction among patients with high EDIC comparing 8% for the low-EDIC group). Patients with intermediate EDIC (6-8 Gy) may have limited benefits unless a substantial reduction of EDIC could be achieved (i.e., 6.0 Gy or less).

The present study is the first to calculated EDIC and demonstrate that EDIC is significantly and strongly associated with local progression-free survival and overall survival among patients with unresectable stage III NSCLC treated with concurrent chemoradiation. The findings indicate that radiation toxicity to the immune system affects treatment outcomes.

What is claimed is:

1. A radiotherapy system comprising a radiotherapy device configured to deliver a radiotherapy to a patient and a treatment controller having one or more processors and a non-transitory, tangible storage medium containing instructions that, when executed, cause the one or more processors to:
    calculate from an initial radiotherapy treatment plan for a patient, an equivalent uniform dose (EUD) for each organ in a target irradiation area in the patient;
    calculate an effective dose of radiation to circulating immune cells in blood (EDIC) for the patient by summing all EUDs for all organs in the target irradiation area; and
    generate a new patient-specific radiotherapy treatment plan for the patient, wherein the new patient-specific radiotherapy treatment plan decreases a calculated EDIC relative to the initial radiotherapy treatment plan, wherein the radiotherapy device is configured to deliver radiotherapy to the patient according to the new patient-specific radiotherapy treatment plan.

2. The radiotherapy system of claim 1, wherein the new patient-specific radiotherapy treatment plan further maximizes a radiation dose to a tumor.

3. The radiotherapy system of claim 2, wherein the new patient-specific radiotherapy treatment plan is generated by adjusting the initial radiotherapy treatment plan by one or more of:
    increasing radiation delivery time;
    adjusting at least one of: beam energies, beam directions, and number of beams;
    optimizing collimator margins;
    dose escalation; and
    increasing margins.

4. The radiotherapy system of claim 1, wherein the new patient-specific radiotherapy treatment plan results in a calculated EDIC of 6.0 Gy or less.

5. The radiotherapy system of claim 1, wherein the new patient-specific radiotherapy treatment plan is generated by adjusting the initial radiotherapy treatment plan by one or more of:
    incorporating a hypofractionated radiotherapy treatment regimen;
    decreasing radiation delivery time;

adjusting at least one of: beam energies, beam directions, and number of beams;
optimizing collimator margins;
incorporating an intensity-modulated radiotherapy planning technique;
incorporating an image-guided adaptive therapy technique;
incorporating a proton therapy technique;
dose de-escalation; and
margin reduction.

6. The radiotherapy system of claim 1, wherein the EUD for each organ is calculated from a dose volume histogram (DVH) for blood circulating through the organ, wherein the DVH after an ith radiation fraction represents a percentage of total body blood volume that receives a particular radiation dose when in the organ during the radiation fractions.

7. The radiotherapy system of claim 1, wherein the EUD for each organ is calculated as a product of a percentage of blood volume B % in an organ, a mean organ dose for the organ, a dose effectiveness factor, and one half a quotient of n and a radiation saturation fraction factor, wherein n is a number of radiation fractions to be administered.

8. The radiotherapy system of claim 1, wherein the EUD for each organ is calculated as a product of a percentage of blood volume B % in an organ and a mean organ dose for the organ, wherein B % is an amount of blood contained in the organ at any time relative to a total body blood volume, a number of radiation fractions to be administered to the patient is equal to or greater than a quotient of a radiation saturation fraction factor and V %, wherein V % is a percentage of blood that receives a radiation dose as the blood passes through the organ.

9. The radiotherapy system of claim 1, wherein the target irradiation area is a thoracic area, and the EDIC is calculated by summing the EUDs for the patient's lungs, heart, thoracic great vessels, and small vessels and capillaries in the thoracic area.

10. The radiotherapy system of claim 1, further comprising one or more imaging modalities.

11. The radiotherapy system of claim 1, wherein the instructions, when executed, cause the one or more processors to generate one or more additional new patient-specific radiotherapy treatment plans for the patient during delivery of the new patient-specific radiotherapy treatment plan to the patient.

12. A method for treating a patient, the method comprising:
calculating from an initial radiotherapy treatment plan for the patient, an equivalent uniform dose (EUD) for each organ in a target irradiation area in the patient;
calculating an effective dose of radiation to circulating immune cells in blood (EDIC) for the patient by summing all EUDs for all organs in the target irradiation area;
generating a new patient-specific radiotherapy treatment plan for the patient, wherein the new patient-specific radiotherapy treatment plan decreases a calculated EDIC relative to the initial radiotherapy treatment plan; and
delivering radiotherapy to the patient according to the new patient-specific radiotherapy treatment plan.

13. The method of claim 12, wherein the new patient-specific radiotherapy treatment plan further maximizes a radiation dose to a tumor.

14. The method of claim 13, wherein the new patient-specific radiotherapy treatment plan is generated by amending the initial radiotherapy treatment plan by one or more of:
increasing radiation delivery time;
adjusting at least one of: beam energies, beam directions, and number of beams;
optimizing collimator margins;
dose escalation; and
increasing margins.

15. The method of claim 12, wherein the new patient-specific radiotherapy treatment plan results in a calculated EDIC of 6.0 Gy or less.

16. The method of claim 12, wherein the new patient-specific radiotherapy treatment plan is generated by adjusting the initial radiotherapy treatment plan by one or more of:
incorporating a hypofractionated radiotherapy treatment regimen;
decreasing radiation delivery time;
adjusting at least one of: beam energies, beam directions, and number of beams;
optimizing collimator margins;
incorporating an intensity-modulated radiotherapy planning technique;
incorporating an image-guided adaptive therapy technique;
incorporating a proton therapy technique;
dose de-escalation; and
margin reduction.

17. The method of claim 12, wherein the EUD for each organ is calculated from a dose volume histogram (DVH) for blood circulating through the organ, wherein the DVH after an ith radiation fraction represents a percentage of total body blood volume that receives a particular radiation dose when in the organ during the radiation fractions.

18. The method of claim 12, wherein the EUD for each organ is calculated as a product of a percentage of blood volume B % in an organ, a mean organ dose for the organ, a dose effectiveness factor, and one half a quotient of n and a radiation saturation fraction factor, wherein n is a number of radiation fractions to be administered.

19. The method of claim 12, wherein the EUD for each organ is calculated as a product of a percentage of blood volume B % in an organ and a mean organ dose for the organ, wherein B % is an amount of blood contained in the organ at any time relative to a total body blood volume, a number of radiation fractions to be administered to the patient is equal to or greater than a quotient of a radiation saturation fraction factor and V %, wherein V % is a percentage of blood that receives a radiation dose as the blood passes through the organ.

20. The method of claim 12, wherein the target irradiation area is a thoracic area, and the EDIC is calculated by summing the EUDs for the patient's lungs, heart, thoracic great vessels, and small vessels and capillaries in the thoracic area.

21. The method of claim 12, further comprising acquiring an image of the target irradiation area in the patient utilizing at least one imaging modality.

22. The method of claim 12, further comprising generating one or more additional new patient-specific radiotherapy treatment plans for the patient during delivery of the new patient-specific radiotherapy treatment plan to the patient, stopping delivery of the new patient-specific radiotherapy treatment plan to the patient, and delivering one of the one or more additional new patient-specific radiotherapy treatment plans.

23. A radiotherapy system comprising a radiotherapy device configured to deliver a radiotherapy in accordance with a radiotherapy plan and one or more processors programmed to perform the two calculating steps and the generating step of the method according to claim 12.

24. A non-transitory computer-readable medium having instructions stored thereon for causing one or more processors to perform the two calculating steps and the generating step of the method according to claim 12.

25. A radiotherapy treatment controller comprising one or more processors and a non-transitory, tangible storage medium containing instructions that, when executed, cause the one or more processors to:
    calculate from an initial radiotherapy treatment plan for a patient, an equivalent uniform dose (EUD) for each organ in a target irradiation area in the patient;
    calculate an effective dose of radiation to circulating immune cells in blood (EDIC) for the patient by summing all EUDs for all organs in the target irradiation area; and
    generate a new patient-specific radiotherapy treatment plan for the patient, wherein the new patient-specific radiotherapy treatment plan decreases a calculated EDIC relative to the initial radiotherapy treatment plan.

26. The radiotherapy treatment controller of claim 25, wherein the radiotherapy treatment controller is communicatively coupled to a radiotherapy device configured to deliver radiotherapy to the patient.

27. The radiotherapy treatment controller of claim 25, wherein the radiotherapy device is configured to deliver the radiotherapy to the patient according to the new patient-specific radiotherapy treatment plan.

28. The radiotherapy treatment controller of claim 25, wherein the new patient-specific radiotherapy treatment plan further maximizes a radiation dose to a tumor.

29. The radiotherapy treatment controller of claim 28, wherein the new patient-specific radiotherapy treatment plan is generated by adjusting the initial radiotherapy treatment plan by one or more of:
    increasing radiation delivery time;
    adjusting at least one of: beam energies, beam directions, and number of beams;
    optimizing collimator margins;
    dose escalation; and
    increasing margins.

30. The radiotherapy treatment controller of claim 25, wherein the new patient-specific radiotherapy treatment plan results in a calculated EDIC of 6.0 Gy or less.

31. The radiotherapy treatment controller of claim 25, wherein the new patient-specific radiotherapy treatment plan is generated by adjusting the initial radiotherapy treatment plan by one or more of:
    incorporating a hypofractionated radiotherapy treatment regimen;
    decreasing radiation delivery time;
    adjusting at least one of: beam energies, beam directions, and number of beams;
    optimizing collimator margins;
    incorporating an intensity-modulated radiotherapy planning technique;
    incorporating an image-guided adaptive therapy technique;
    incorporating a proton therapy technique;
    dose de-escalation; and
    margin reduction.

32. The radiotherapy treatment controller of claim 25, wherein the EUD for each organ is calculated from a dose volume histogram (DVH) for blood circulating through the organ, wherein the DVH after an ith radiation fraction represents a percentage of total body blood volume that receives a particular radiation dose when in the organ during the radiation fractions.

33. The radiotherapy treatment controller of claim 25, wherein the EUD for each organ is calculated as a product of a percentage of blood volume B % in an organ, a mean organ dose for the organ, a dose effectiveness factor, and one half a quotient of n and a radiation saturation fraction factor, wherein n is a number of radiation fractions to be administered.

34. The radiotherapy treatment controller of claim 25, wherein the EUD for each organ is calculated as a product of a percentage of blood volume B % in an organ and a mean organ dose for the organ, wherein B % is an amount of blood contained in the organ at any time relative to a total body blood volume, a number of radiation fractions to be administered to the patient is equal to or greater than a quotient of a radiation saturation fraction factor and V %, wherein V % is a percentage of blood that receives a radiation dose as the blood passes through the organ.

35. The radiotherapy treatment controller of claim 25, wherein the target irradiation area is a thoracic area, and the EDIC is calculated by summing the EUDs for the patient's lungs, heart, thoracic great vessels, and small vessels and capillaries in the thoracic area.

* * * * *